United States Patent
Kellar et al.

(10) Patent No.: US 10,383,339 B2
(45) Date of Patent: Aug. 20, 2019

(54) COMPOSITIONS AND METHODS FOR TREATING PESTS

(71) Applicant: NOVOZYMES BIOAG A/S, Bagsvaerd (DK)

(72) Inventors: Kenneth Edmund Kellar, Durham, NC (US); Emily Looze, Bedford, VA (US); Jarrod Leland, Blacksburg, VA (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 0 days.

(21) Appl. No.: 15/034,642

(22) PCT Filed: Nov. 5, 2014

(86) PCT No.: PCT/US2014/064042
§ 371 (c)(1),
(2) Date: May 5, 2016

(87) PCT Pub. No.: WO2015/069708
PCT Pub. Date: May 14, 2015

(65) Prior Publication Data
US 2016/0270407 A1    Sep. 22, 2016

Related U.S. Application Data

(60) Provisional application No. 61/901,880, filed on Nov. 8, 2013.

(51) Int. Cl.
*A01N 63/04*    (2006.01)
*A01N 25/30*    (2006.01)

(52) U.S. Cl.
CPC ............ *A01N 63/04* (2013.01); *A01N 25/30* (2013.01); *Y02A 50/356* (2018.01)

(58) Field of Classification Search
None
See application file for complete search history.

(56) References Cited

U.S. PATENT DOCUMENTS

| | | | |
|---|---|---|---|
| 5,413,784 A | 5/1995 | Wright | |
| 5,472,493 A * | 12/1995 | Regan | ................ C09D 7/1225 |
| | | | 106/481 |
| 5,512,280 A * | 4/1996 | Johal | ................ A01N 63/04 |
| | | | 424/93.5 |
| 5,516,513 A | 5/1996 | Wright | |
| 5,730,973 A | 3/1998 | Morales | |
| 5,888,989 A | 3/1999 | Kern | |
| 5,939,065 A | 8/1999 | Bradley | |
| 7,241,612 B2 | 7/2007 | Shapiro-Ilan | |
| 2008/0175930 A1* | 7/2008 | Baseeth | ................ A01N 25/30 |
| | | | 424/742 |
| 2010/0112060 A1 | 5/2010 | Maor | |
| 2012/0039976 A1 | 2/2012 | Stamets | |

FOREIGN PATENT DOCUMENTS

| | | | |
|---|---|---|---|
| CN | 101273729 B * | 6/2011 | |
| DE | 19707178 A1 | 8/1998 | |
| EP | 0406103 B1 | 2/1996 | |
| EP | 1695625 A1 | 8/2006 | |
| EP | 1884160 A1 | 2/2008 | |
| GB | 2255018 A | 10/1992 | |
| WO | 95/10597 A1 | 4/1995 | |
| WO | 02/087344 A1 | 11/2002 | |
| WO | 2008/062413 A2 | 5/2008 | |
| WO | 2008/065413 A1 | 6/2008 | |
| WO | WO 2011032892 A1 * | 3/2011 | ............ A01N 31/02 |
| WO | 2011/099022 A1 | 8/2011 | |

OTHER PUBLICATIONS

Zimmerman 1993 (The Entomopathogenic Fungus *Metarhizium anisopliae* and its Potential as a Biocontrol Agent; Pestic. Sci. 37: 375-379).*
Nematodes: Alternative Controls (2006) by Martine Guerena; an ATTRA publication; pp. 1-20 (Year: 2006).*
Ngakou et al, 2008, Crop Protect 27 (3-5), 481-488.

* cited by examiner

*Primary Examiner* — Mary Maille Lyons
(74) *Attorney, Agent, or Firm* — Todd Sladek

(57) ABSTRACT

Disclosed herein are pest controlling compositions (i.e., biopesticides) comprising one or more entomopathogenic fungi which. Further disclosed are methods of using such compositions for controlling invasive pests, particularly agriculturally relevant pests.

9 Claims, No Drawings

COMPOSITIONS AND METHODS FOR TREATING PESTS

CROSS-REFERENCE TO RELATED APPLICATIONS

This application is a National Stage of International Application No. PCT/US2014/064042, filed Nov. 5, 2014, which claims priority to U.S. Provisional Application No. 61/901,880, filed Nov. 8, 2013.

FIELD OF THE INVENTION

Disclosed herein are insect control compositions comprising entomopathogenic fungi, and methods of using such compositions for controlling crop damaging pests in agricultural environments.

BACKGROUND OF THE INVENTION

Pests, such as insects, Acari (mites and ticks) and nematodes, are a major problem for the agriculture industry, limiting productivity, often significantly. Although chemical pesticides are used to control pests, excessive use of chemical pesticides leaves residues in soil, water and air and also has adverse effects on the non-target organisms and the ecological balance. In addition, pests can develop resistance to chemical pesticides, limiting their effectiveness and application. Public concern over potential health hazards of chemical pesticides and the increase in cost of chemical pesticides has also led to the exploration of more eco-friendly pest management tactics.

Biopesticides have been developed for use as an alternative, or in some cases as a supplement, to chemical pesticides. Biopesticides are living organisms (e.g., fungi and bacteria) that intervene in the life cycle of pests (by killing or disabling the pest). Examples of biopesticides include the entomopathogenic fungus *Metarhizium anisopliae*, which has been registered as a bio-insecticide for the control of insect pests in the United States and many other countries. *Metarhizium anisopliae* has been reported to infect many insect types including subterranean termites (*Reticulitermes* and *Coptotermes* spp.), corn rootworms (*Diabrotica* spp), black vine weevils (*Otiorhynchus sulcatus*), citrus root weevils (*Diaprepes abbreviatus*), Japanese beetles (*Popillia japonica*), and European chafers (*Rhizotrogus majalis*).

As natural agents, biopesticides offer more eco-friendly solutions for controlling pests and/or for use in combination with chemical pesticide. However, drawbacks of using biopesticides include effective delivery to area to be treated and the potential phytotoxic effects of formulations on crops and plants. Often biopesticides can clog nozzles on delivery devices and/or adhere to the inner surfaces of a delivery tank (often referred to as "staining") because some biopesticides (e.g., *Metarhizium* spp.) are insoluble hydrophobic particles. Solutions have been to include surfactants in biopesticides formulations; however, many surfactants have been found to have phytotoxic effects on plants—including those of major agricultural importance.

An important need exists for biopesticides formulations which have low phytotoxic effects on plants and are efficiently delivered and do not clog nozzles or adhere to the inner surfaces of delivery devices when being applied.

EP Patent No.: 0406103 discloses pesticidal compositions base on microorganisms, processes for their preparation, and their use in agronomy.

GB Patent No.: 2,255,018 discloses entomopathogenic sprays and methods of controlling insects.

U.S. Patent Application Publication No.: 2012/0039976 discloses utilizing extracts of the pre-sporulation (pre-conidia) mycelia stage of entomopathogenic fungi as insect and arthropod attractants and/or pathogens.

Published PCT Patent Application No.: WO 95/10597 discloses entomopathogenic formulations that include conidia of an entomopathogenic fungus and a carrier. Methods of killing insects such as grasshoppers using the disclosed formulations are described.

Published PCT Patent Application No.: WO 08/065413 discloses formulations of entomopathogenic fungi for insect control.

U.S. Pat. No. 5,888,989 discloses insecticidal and acaricidal compositions of silafluofen and at least one entomopathogenic fungus, such as, for example, *Beauveria bassiana.*

U.S. Pat. No. 5,512,280 discloses maintenance and long term stabilization of fungal conidia using surfactants.

EP Patent Application Publication No.: 1,884,160 discloses biopesticide compositions comprising fungal spores pathogenic for tics, tween, and paraffin oil.

U.S. Patent Application Publication No.: 2010/0112060 describes insecticidal compositions comprising spores of entomopathogenic fungi suspended in oil in water emulsions comprising fatty acid salts, polyhydric alcohols, and additional emulsifiers. The publication further describes methods for using the compositions for preventing and controlling insect infestation in animals and natural areas—in particular, tick infestations are disclosed.

German Patent Application Publication No.: DE 19707178 discloses insecticidal or acaricidal compositions.

Published PCT Patent Application No.: WO 11/099022 discloses compositions and methods of preparing the composition and methods for preparing fungal based products from innovative combination of dormant spore of naturally occurring *Metarhizium anisopliae, Beauveria bassiana* and *Verticillium lecanii* fungus with enzymes, fats and growth promoting molecules. Uses for controlling pests like aphids, whitefly, thrips, mite, jassids, Mealybug, and caterpillars and as well as soil borne insects like white grub, termite and alike are also disclosed.

U.S. Pat. No. 5,413,784 describes a novel and useful biopesticides with activity against insect pests such as boll weevil, sweet potato whitefly, and cotton fleahopper. The biopesticides comprises an entomopathogenic fungus having virulence against targets insect pests. A preferred fungus is *Beauveria bassiana* ATCC-7040.

U.S. Pat. No. 5,939,065 describes an entomopathogenic fungus having virulence against insects of the grasshopper family. The fungus is a strain of *Beauveria bassiana*—specifically *B. bassiana* BbGHA1991, ATTC 72450.

U.S. Pat. No. 5,516,513 describes an agricultural formulation of a virulent isolate of *Beauveria bassiana*, which has the characteristics of *B. bassiana* ATCC 74040, can be used to effectively control lepidopterous insects. This fungal strain has been found to be active against the egg stage of lepidopterans. Activity against the larval stages of lepidopterans is also shown.

U.S. Pat. No. 7,241,612 describes a biopesticidal composition for controlling insects (e.g., pecan weevils, the diaprepes root weevil, fall armyworm, fire ants), containing an agriculturally acceptable carrier and an effective insect (e.g., pecan weevils, the *diaprepes* root weevil, fall armyworm, fire ants) biopesticidal amount of a fungus selected from the group consisting of *Beauveria bassiana* having the identifying characteristics of *Beauveria bassiana* NRRL 30593, *Metarhizium anisopliae* having the identifying characteristics of *Metarhizium anisopliae* NRRL 30594, *Beauveria bassiana* having the identifying characteristics of *Beauveria bassiana* NRRL 30601, *Beauveria bassiana* having the identifying characteristics of *Beauveria bassiana* NRRL 30600, or mixtures thereof. Also, a method for controlling insects (e.g., pecan weevils, the *diaprepes* root weevil, fall armyworm, fire ants), involving applying an effective insect biopesticidal amount of the composition to the insects or to the plants, areas or substrates infested with the insects.

While many solutions exist to control a variety of insect pests, a need remains for a formulation that will not only control insect pests, but one which can be efficiently delivered without having phytotoxic effects on plants when the formulation is applied. A formulation capable of being efficiently applied (e.g., without clogging and/or adherence of actives and/or other excipients to surfaces, etc.) to control pests, while having minimal, if any, environmental impact or phytotoxic effects, is highly desirable.

SUMMARY OF THE INVENTION

The inventors found, that fungal spore formulations, which are often suspended in oil, do not disperse well when diluted with water. Without being bound by theory, it is believed that if the oil phase is poorly dispersed, oil droplets will increase in size and the hydrophobic fungal spores will be attracted to the droplets and/or locate entirely inside the oil droplets. These droplets are attracted to the inner walls/surfaces of sprayer tanks (i.e., especially plastic containers often used in the agricultural industry) causing poor and inefficient dispersion of the actives (e.g., the fungal spores), clogging of the spraying equipment (e.g., the nozzles or hoses), and difficulty in cleaning tanks and other spray or delivery equipment. To eliminate this problem, a variety of surfactant systems were applied; however, phytotoxicity remains a problem. The inventors discovered, surprisingly and unexpectedly, that the proper combination of surfactants at particular ratios, often very small amounts of one surfactant relative to another, would decrease the overall phytotoxicity of a particular formulation while simultaneously overcoming known challenges encountered when trying to adequately deliver the active ingredients when diluted with water and applied.

The problem to be solved by the biopesticides (i.e., compositions) described herein can be depicted accordingly.

TABLE 1

Surfactant amount related to phytotoxicity and residue formation.

| Low wt. % of one or more surfactants in biopesticide | Optimal wt. % of one or more surfactants in biopesticide | High wt. % of one or more surfactants in biopesticide |
|---|---|---|
| Highest phytotoxicity | Acceptable phytoxicity | Lowest phytotoxicity |
| Least residues on plastic, poor delivery of biopesticide | Acceptable residues on plastic | Most residues on plastic |

Accordingly, disclosed herein are biopesticides (i.e., compositions) and methods which offer an improved and practical approach to controlling damage caused to crops by pest populations. The biopesticides described herein will have the benefit of controlling pests but also have the added benefits of being efficiently delivered when fully formulated (i.e., actives and/or other excipients will not be retained within the inside of a holding tank, e.g., reduced adherence/sticking of actives and/or other excipients to the inner surfaces of the a tank, or clog the delivery apparatus or parts thereof e.g., the nozzles or hoses of the delivery device) and cause minimal, if any, phytotoxic injury to the crops treated with the fully formulated biopesticide.

The biopesticide will comprise an agriculturally suitable carrier, a pesticidally effective amount of at least one fungal pesticide, and at least one surfactant. In a particular embodiment, the agriculturally suitable carrier is oil. In an even more particular embodiment, the oil is a paraffinic oil. Particular fungal pesticides include entomopathogenic fungi, including species of *Ascomycota, Alternaria, Beauveria, Lecanicillium, Metarhizium, Verticillium, Trichoderma, Aspergillus, Nomuraea, Paecilomyces, Isaria, Hirsutella, Fusarium, Cordyceps, Entomophthora, Zoophthora, Pandora, Entomophaga, Entomophthorales* and *Zygomycota*. In a particular embodiment, the biopesticides comprises the fungal pesticide *Metarhizium anisopliae* (sometimes referred to as *Metarhizium brunneum*). Further, the biopesticides described herein comprise at least one surfactant selected from sorbitan fatty esters, sorbitol ethoxylates esters, alcohol ethoxylates, and combinations thereof. In an even more particular embodiment, the at least one surfactant comprises a mixture of a sorbitan monostearate and a polyoxyethylene sorbitol hexaoleate. In another particular embodiment, the at least one surfactant may comprise a mixture of a sorbitan monooleate and a polyoxyethylene sorbitol hexaoleate. In another particular embodiment, the at least one surfactant may comprise a mixture of a sorbitan monostearate, a sorbitan monooleate and a polyoxyethylene sorbitol hexaoleate. In another particular embodiment, the at least one surfactant may comprise a mixture of a sorbitan monostearate and a sorbitan monooleate.

The biopesticides described herein may further comprise an anti-settling agent. In a particular embodiment, the anti-settling agent comprises a fumed silica.

In still another embodiment, the biopesticide described herein comprises an agriculturally suitable carrier, wherein the carrier comprises a paraffinic oil, at least one fungal pesticide, wherein the at least one fungal pesticide comprises *Metarhizium anisopliae*, at least one surfactant wherein the at least one surfactant comprises a mixture of a sorbitan monostearate and a polyoxyethylene sorbitol hexaoleate, and an anti-settling agent, wherein the anti-settling agent comprises a fumed silica. The sorbitan monostearate may be substituted with a sorbitan monooleate.

In an embodiment, additional agriculturally beneficial ingredients (e.g., beneficial microbes, signal molecules, insecticides, fungicides, nematicides, and combinations thereof) may also be used in combination with the biopesticides described herein, including as part of the same composition or applied as a separate treatment.

Disclosed herein are also methods for controlling pests. In an embodiment, the method comprises contacting one or more plant pest with a biopesticide comprising an agriculturally suitable carrier, a pesticidally effective amount of at least one fungal pesticide, and at least one surfactant wherein the at least one surfactant is selected from sorbitan fatty esters, sorbitol ethoxylates esters, alcohol ethoxylates and combinations thereof.

Further disclosed are seeds coated with a biopesticide comprising an agriculturally suitable carrier, a pesticidally effective amount of at least one fungal pesticide, and at least one surfactant wherein the at least one surfactant is selected from sorbitan fatty esters, sorbitol ethoxylates esters, alcohol ethoxylates, and combinations thereof.

DETAILED DESCRIPTION OF THE INVENTION

The disclosed embodiments relate to compositions and methods for controlling pests.

Definitions

As used herein, the singular forms "a", "an" and "the" are intended to include the plural forms as well, unless the context clearly indicates otherwise.

As used herein, the terms "active", "active ingredient", "agricultural active ingredient", etc. mean any biological organism or chemical element, molecule, or compound, or mixture thereof, which has a biological activity in a seed, a plant, or a disease or pest of a seed or plant. Such active ingredients include, but are not limited to, pesticides, herbicides, fertilizers, plant growth regulators, drugs, dyes, biological attractants, scents and pheromones.

As used herein, the term "carrier" is intended to refer to an "agronomically acceptable carrier." An "agronomically acceptable carrier" is intended to refer to any material which can be used to deliver the actives (e.g., microorganisms described herein, agriculturally beneficial ingredient(s), biologically active ingredient(s), etc.) to a plant or a plant part (e.g., plant foliage), and preferably which carrier can be applied (to the plant, plant part (e.g., foliage, seed), or soil) without having an adverse effect on plant growth, soil structure, soil drainage or the like.

As used herein, the term "soil-compatible carrier" is intended to refer to any material which can be added to a soil without causing/having an adverse effect on plant growth, soil structure, soil drainage, or the like.

As used herein, the term "seed-compatible carrier" is intended to refer to any material which can be added to a seed without causing/having an adverse effect on the seed, the plant that grows from the seed, seed germination, or the like.

As used herein, the term "foliar-compatible carrier" is intended to refer to any material which can be added to a plant or plant part without causing/having an adverse effect on the plant, plant part, plant growth, plant health, or the like.

As used herein, the term "fungal pesticide" means a fungal organism, whether in a vegetative state or a dormant state (e.g., spore), that is pathogenic to a target pest, such as, an insect, Acari, or a nematode. As used herein, the terms "spore" has its normal meaning which is well known and understood by those of skill in the art and refers to a microorganism in its dormant, protected state.

As used herein, the term "entomopathogenic" means that the fungal pesticide is pathogenic to at least one target insect. As used herein, "entomopathogenic fungus" is a fungus that is capable of attacking, infecting, killing, disabling, causing disease, and/or causing injury to an insect, and is thus able to be used in the control insect infestation by adversely affecting the viability or growth of the target insect.

As used herein, the term "acaripathogenic" means that the fungal pesticide is pathogenic to at least one target Acari, such as, as mite or tick. As used herein, "acaripathogenic fungus" is a fungus that is capable of attacking, infecting, killing, disabling, causing disease, and/or causing injury to an Acari, and is thus able to be used in the control of Acari infestation by adversely affecting the viability or growth of the target Acari.

As used herein in, a "cuticle degrading enzyme" is an enzyme that is able to at least partially degrade a cuticle of a pest, such as, the epicuticle and/or the procuticle. The exogenously applied cuticle degrading enzyme can increase the efficacy of the fungal pesticide by increasing the ability of the fungal pesticide to colonize and/or or bore through the pest's cuticle to reach the pest's body cavity.

As used herein, "exogenously applied" means that the cuticle degrading enzyme is applied independently (that is, as a separate ingredient) from the compositions disclosed herein and any enzyme produced by fungal pesticide.

The "exogenously applied" cuticle degrading enzyme is in the form of an "isolated" enzyme composition.

The term "isolated" means the enzyme is in a form or environment which does not occur in nature, that is, the enzyme is at least partially removed from one or more or all of the naturally occurring constituents with which it is associated in nature. Thus, although enzymes produced endogenously by the fungal pesticide will impact efficacy, an isolated enzyme does not encompass an enzyme endogenously produced by the fungal pesticide during treatment of a pest in the processes of the present invention. An isolated enzyme may be present in the form of a purified enzyme composition or a fermentation broth sample that contains the enzyme.

The term "pest" refers to any animal of the scientific classification (phylum) Arthropoda including Insecta, (e.g., white flies, thrips, weevils) and Arachnida, which includes but is not limited to, mites, ticks, spiders, and other like invertebrates.

As used herein, the term "control" or "controlling" as in e.g., the phrase: the "control" of pests or pest populations, or "controlling" pests or pest populations, or as in the phrase: "controlling" pests, refers to preventing, reducing, killing, inhibiting the growth of, or elimination of a pest or population of pests as defined herein. Indeed, "control" or "controlling" as used herein refers to any indicia of success in prevention, killing, inhibition, elimination, reduction or amelioration of a pest or pest population.

As used herein, the terms "effective amount", "effective concentration", or "effective dosage" are defined as the amount, concentration, or dosage of the fungal pesticide sufficient to cause infection in the pest which will then lead to the controlling of pests. The actual effective dosage in absolute value depends on factors including, but not limited to, the mortality rate of the target pests relative to the rate at which the fungal pesticide is applied, synergistic or antagonistic interactions between the other active or inert ingredients which may increase or reduce the activity of the fungal pesticide, the inherent susceptibility of the life stage and species of pest, and the stability of the fungal pesticide in compositions. The "effective amount", "effective concentration", or "effective dosage" of the fungal pesticide may be determined, e.g., by a routine dose response experiment.

As used herein, the term "agriculturally beneficial ingredient(s)" is intended to mean any agent or combination of agents capable of causing or providing a beneficial and/or useful effect in agriculture. As used herein, the term "agriculturally beneficial microorganism(s)", "agriculturally beneficial microbe", "agriculturally beneficial bacteria", etc. is intended to mean any microorganism (e.g., bacteria, fungus, etc., or combination thereof), regardless of whether the microorganism is in a vegetative state or spore form, that is capable of causing or providing a beneficial and/or useful effect in agriculture (e.g., enhancing plant growth, providing fungicidal activity, etc.).

As used herein, the term "nitrogen fixing organism(s)" is intended to refer to any organism capable of converting atmospheric nitrogen ($N_2$) into ammonia ($NH_3$).

As used herein, the term "phosphate solubilizing organism" is intended to refer to any organism capable of converting insoluble phosphate into a soluble phosphate form.

As used herein, the terms "spore", "microbial spore", etc., has its normal meaning which is well known and understood by those of skill in the art. As used herein, the terms "spore" and "microbial spore" refer to a microorganism in its dormant, protected state.

As used herein, the term "inoculum" is intended to mean any form of microbial cells, or spores, which is capable of propagating on or in the soil when the conditions of temperature, moisture, etc., are favorable for microbial growth.

As used herein, the term "isomer(s)" is intended to include all stereoisomers of the compounds and/or molecules referred to herein (e.g., flavonoids, LCOs, COs, chitinous compounds, jasmonic acids, linoleic acids, linolenic acids, kerrikins, or derivatives of any molecules thereof, etc.), including enantiomers, diastereomers, as well as all conformers, roatmers, and tautomers, unless otherwise indicated. The compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers, and tautomers of compounds and/or molecules depicted.

As used herein, the terms "plant(s)" and "plant part(s)" are intended to refer to all plants and plant populations such as desired and undesired wild plants or crop plants (including naturally occurring crop plants). Crop plants can be plants, which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material and vegetative and generative propagation material (e.g., cuttings, tubers, rhizomes, off-shoots and seeds, etc.).

As used herein, the term "foliage" is intended to mean all parts and organs of plants above the ground. Non-limiting examples include leaves, needles, stalks, stems, flowers, fruit bodies, fruits, etc. As used herein, the term "foliar application", "foliarly applied", and variations thereof, is intended to include application of an active ingredient to the foliage or above ground portions of the plant, (e.g., the leaves of the plant). Application may be effected by any means known in the art (e.g., spraying the active ingredient).

As used herein, the term "source" of a particular element is intended to mean a compound of that element which, at least in the soil conditions under consideration, does not make the element fully available for plant uptake.

As used herein, the term "nutrient(s)" is intended to refer to any nutrient (e.g., vitamins, macrominerals, micronutrients, trace minerals, organic acids, etc.) which are needed for plant growth, plant health, and/or plant development.

As used herein, the term "herbicide(s)" is intended to refer to any agent or combination of agents capable of killing weeds and/or inhibiting the growth of weeds (the inhibition being reversible under certain conditions).

As used herein, the term "fungicide(s)" is intended to refer to any agent or combination of agents capable of killing fungi and/or inhibiting fungal growth.

As used herein, the term "insecticide(s)" is intended to refer to any agent or combination of agents capable of killing one or more insects and/or inhibiting the growth of one or more insects.

As used herein, the term "nematicide(s)" is intended to refer to any agent or combination of agents capable of killing one or more nematodes and/or inhibiting the growth of one or more nematodes.

As used herein, the term "acaricide(s)" is intended to refer to any agent or combination of agents capable of killing one or more acarids and/or inhibiting the growth of one or more acarids.

As used herein, the term "biostimulant(s)" is intended to refer to any agent or combination of agents capable of enhancing metabolic or physiological processes within plants and soils.

As used throughout this specification, the terms "parts by weight" or "percentage weight" are used interchangeably in the specification wherein the weight percentages of each of the individual constituents are indicated in weight percent based on the total weight of the particular composition of which it forms a part.

Biopesticides (Compositions):

The biopesticides (i.e., the compostisions) used in the embodiments disclosed herein comprise an agriculturally suitable carrier, a pesticidally effective amount of at least one fungal pesticide (e.g., as in two or more, such as two, three, four, five, six, seven, eight, nine, ten, etc.), and at least one surfactant (e.g., as in two or more, such as two, three, four, five, six, seven, eight, nine, ten, etc.). In a particular embodiment, the at least one surfactant is selected from sorbitan fatty esters, sorbitol ethoxylates esters, alcohol ethoxylates and combinations thereof.

The biopesticides described herein will have the benefit of controlling pests but also have the added benefits of being efficiently delivered when fully formulated (i.e., the actives and/or other excipients will not be retained within the inside of a holding tank, e.g., reduced adherence/sticking of actives and/or other excipients to the inner surfaces of the a tank, or clog the delivery apparatus or parts thereof, e.g., the nozzles or hoses of the delivery device) and cause minimal, if any, phytotoxic injury to the crops treated with the fully formulated biopesticide. As used herein, an agent is "phytotoxic" if it causes harm or damage to a plant or seed with which it comes in contact. Plant and seed damage or harm includes, for example, stunting, chemical burning, yield depression, malformation, discoloration, lack of germination, reduction in germination rate, death, and the like.

The fungal pesticides compositions described herein can be of any form so long as the composition is able to support the desired activity (effective amount) of the fungal pesticide, regardless of form (e.g., vegetative state or dormant state), and the composition can be applied to control a target pest. The carrier may be used to provide an environment to support the viability of the at least one fungus, including by providing the proper environmental conditions and protecting the fungal pesticide from harmful environmental conditions (e.g., excess oxygen, moisture and/or ultraviolet radiation, etc.). Unless the compositions are generated immediately prior to use, the carrier may be used to maintain the activity of the fungal pesticide during storage (e.g., in a container for the entire shelf-life of the formulated product). The carrier may also be used to maintain the activity of the fungal pesticide after the fungal pesticide compositions described throughout have been applied to the application surface. In particular embodiments, the carrier provides an environment such that the fungal pesticide will not have more than a 1-log loss of the original viable content (prior to including in a carrier) over at least a one year period. Further still, the fungal pesticides described herein are transferable from the carrier to the body of the target pest (e.g., white flies, thrips, mites, weevils, ticks, chinch bugs, etc.).

In certain embodiments, the biopesticide may be in the form of a gel, a foam, a solid (such as a powder, granule, particle, etc.), or a liquid. In a particular embodiment, the biopesticide is in the form of a liquid. In a more particular embodiment, the biopesticide is in the form of a liquid suspension. In an even more particular embodiment, the biopesticide is in the form of a liquid non-aqueous suspension.

Carrier(s):

The carrier will have the required values (and range of values) from rheological measurements (e.g., viscosity, yield value, storage modulus, and loss modulus) to allow the fungal pesticide to remain efficacious (e.g., able to be transferred to the body of the pest with a degree of lethality, prevent settling of the fungal pesticide, allow the biopesticide to be easily redispursed and dispensed into a tank, such as a water tank, etc.) and viable once formulated.

In an embodiment, the biopesticide (i.e., the composition), may be formed of 0.01 wt. % to 99.99 wt. % of carrier. There may be minor variances when measuring the weight percentage of the carrier and the biopesticide may be formed of about 0.01 wt. % to about 99.99 wt. % of carrier. In still another embodiment, the biopesticide may be formed of 50.00 wt. % to 99.99 wt. % of carrier. Again, there may be minor variances when measuring the weight percentage of the carrier and the biopesticide may be formed of about 50.00 wt. % to about 99.99 wt. % of carrier. In still yet another embodiment, the biopesticide is formed of 50.00 wt. % to 80.00 wt. % of carrier. Yet again, there may be minor variances when measuring the weight percentage of the carrier and the biopesticide may be formed of about 50.00 wt. % to about 80.00 wt. % of carrier. Therefore, in embodiments of the biopesticides disclosed herein, the total amount of carrier may be as low as 0.01 wt. % and as high as 99.99 wt. % (e.g., between 0.01 and 99.99 wt. %). In other embodiments the total amount of the agriculturally suitable/acceptable carrier may be between about 57-55 wt. %, 58-54 wt. %, 59-53 wt. %, 60-52 wt. %, 62-50 wt. %, 64-48 wt. %, 66-46 wt. %, 68-44 wt. %, 70-42 wt. %, 72-40 wt. %, and the like.

In a particular embodiment, the biopesticide is formed of 80.50 wt. % of carrier. There may be minor variances when measuring the weight percentage of the carrier and the biopesticide may be formed of about 80.50 wt. % of carrier. In another particular embodiment, the biopesticide is formed of 80.00 wt. % of carrier. There may be minor variances when measuring the weight percentage of the carrier and the biopesticide may be formed of about 80.00 wt. % of carrier. In still another particular embodiment, the biopesticide is formed of 78.00 wt. % of carrier. There may be minor variances when measuring the weight percentage of the carrier and the biopesticide may be formed of about 78.00 wt. % of carrier. In yet another particular embodiment, the biopesticide is formed of 75.50 wt. % of carrier. There may be minor variances when measuring the weight percentage of the carrier and the biopesticide may be formed of about 75.50 wt. % of carrier. In still yet another particular embodiment, the biopesticide is formed of 75.00 wt. % of carrier. There may be minor variances when measuring the weight percentage of the carrier and the biopesticide may be formed of about 75.00 wt. % of carrier. In yet still another particular embodiment, the biopesticide is formed of 73.00 wt. % of carrier. There may be minor variances when measuring the weight percentage of the carrier and the biopesticide may be formed of about 73.00 wt. % of carrier. In another particular embodiment, the biopesticide is formed of 70.50 wt. % of carrier. There may be minor variances when measuring the weight percentage of the carrier and the biopesticide may be formed of about 70.50 wt. % of carrier. In still another particular embodiment, the biopesticide is formed of 70.00 wt. % of carrier. There may be minor variances when measuring the weight percentage of the carrier and the biopesticide may be formed of about 70.00 wt. % of carrier. In yet another particular embodiment, the biopesticide is formed of 68.00 wt. % of carrier. There may be minor variances when measuring the weight percentage of the carrier and the biopesticide may be formed of about 68.00 wt. % of carrier. In still yet another particular embodiment, the biopesticide is formed of 66.00 wt. % of carrier. There may be minor variances when measuring the weight percentage of the carrier and the biopesticide may be formed of about 66.00 wt. % of carrier. In yet still another particular embodiment, the biopesticide is formed of 64.00 wt. % of carrier. There may be minor variances when measuring the weight percentage of the carrier and the biopesticide may be formed of about 64.00 wt. % of carrier. In another particular embodiment, the biopesticide is formed of 63.00 wt. % of carrier. There may be minor variances when measuring the weight percentage of the carrier and the biopesticide may be formed of about 63.00 wt. % of carrier. In still another particular embodiment, the biopesticide is formed of 61.00 wt. % of carrier. There may be minor variances when measuring the weight percentage of the carrier and the biopesticide may be formed of about 61.00 wt. % of carrier. In yet another particular embodiment, the biopesticide is formed of 59.00 wt. % of carrier. There may be minor variances when measuring the weight percentage of the carrier and the biopesticide may be formed of about 59.00 wt. % of carrier. In still yet another particular embodiment, the biopesticide is formed of 58.00 wt. % of carrier. There may be minor variances when measuring the weight percentage of the carrier and the biopesticide may be formed of about 58.00 wt. % of carrier. In yet still another particular embodiment, the biopesticide is formed of 56.00 wt. % of carrier. There may be minor variances when measuring the weight percentage of the carrier and the biopesticide may be formed of about 56.00 wt. % of carrier. In other embodiments, the biopesticide may be formed in about 70, 62, 60, 57, 55, 54, 53, 52, 51, 50, 48, 46, 44, 42 wt. % of carrier, or the like. In one embodiment of the composition, the carrier may be a liquid (e.g., aqueous or non-aqueous). In another embodiment of the composition, the carrier may be an aqueous liquid (e.g., water, sugar water (i.e., water containing sucrose, maltose, etc.), etc.).

In a particular embodiment, the carrier is a non-aqueous liquid (e.g., an oil, etc.). The non-aqueous liquid may be a biodegradable non-aqueous liquid. The non-aqueous liquid may be a "Low Vapor Pressure Volatile Organic Compounds (LVP-VOC)," which is a chemical "compound" or "mixture of compounds" containing (1) a vapor pressure less than 0.1 mm Hg at 20° C., (2) composed of chemical compounds with more than 12 carbon atoms and/or (3) a boiling point greater than 216° C. See the definition of LVP-VOC provided by the California Air Resources Board (CARB). The non-aqueous liquid may be a biodegradable LVP-VOC non-aqueous liquid.

Non-limiting examples of non-aqueous liquids suitable as a carrier for the compositions described herein include silicone oils, paraffinic/parrafin oils, mineral oils, vegetable oils, hexylene glycol, glycerol, linoleic acid, oleic acid, and any combination thereof. Non-limiting examples of a commercial mineral/paraffinic oils include BRITOL 50 (available from Sonneborn, Inc., Mahwah, N.J.), Ultra-Fine Spray oil (available from Sunoco, Petronas Lubricants, Belgium Nev.), SunSpray 6N oil (available from Sunoco, Petronas Lubricants, Belgium Nev.), SunSpray 7E Range oil (available from Sunoco, Petronas Lubricants, Belgium Nev.), SunSpray 7N oil, (available from Sunoco, Petronas Lubricants, Belgium Nev.), SunSpray 11E Range oil (available from Sunoco, Petronas Lubricants, Belgium Nev.), SunSpray 11N oil (available from Sunoco, Petronas Lubricants, Belgium Nev.), Banana Spray oil (available from Sunoco, Petronas Lubricants, Belgium Nev.), and BioSpray oil (available from Sunoco, Petronas Lubricants, Belgium Nev.). An example of silicone oil is DM Fluid 100 CS (available from Shin-Etsu Chemical Co., LtD., Tokyo, Japan).

In a particular embodiment, the carrier comprises one or more paraffinic oils. In a more particular embodiment the carrier comprises SunSpray 6N oil (available from Sunoco, Petronas Lubricants, Belgium Nev.).

Fungal Pesticide(s):

Any suitable fungal pesticide may be used, based on the targeted pest. Fungal pesticides are well known in the art. In one embodiment, the fungal pesticide may be one or more entomopathogenic fungi, one or more acaripathogenic fungi, or a combination thereof.

In an embodiment, the biopesticide (i.e., the composition), may be formed of 0.01 wt. % to 30.00 wt. % of fungal pesticide. There may be minor variances when measuring the weight percentage of the fungal pesticide and the biopesticide may be formed of about 0.01 wt. % to about 30.00 wt. % of fungal pesticide. In still another embodiment, the biopesticide may be formed of 1.00 wt. % to 15.00 wt. % of fungal pesticide. Again, there may be minor variances when measuring the weight percentage of the fungal pesticide and the biopesticide may be formed of about 1.00 wt. % to about 15.00 wt. % of fungal pesticide. In still yet another embodiment, the biopesticide is formed of 5.00 wt. % to 11.00 wt. % of fungal pesticide. Yet again, there may be minor variances when measuring the weight percentage of the fungal pesticide and the biopesticide may be formed of about 5.00 wt. % to about 11.00 wt. % of fungal pesticide. Therefore, in embodiments of the biopesticides disclosed herein, the total amount of fungal pesticide may be as low as 0.01 wt. % and as high as 30.00 wt. % (e.g., between 0.01 and 30.00 wt. %). In other embodiments, the wt. % of the fungal pesticide may be between about 10-12, 8-14, 6-16, 4-18, or the like.

In a particular embodiment, the biopesticide is formed of 11.00 wt. % of fungal pesticide. There may be minor variances when measuring the weight percentage of the fungal pesticide and the biopesticide may be formed of about 11.00 wt. % fungal pesticide. In other embodiments, the wt. % of the fungal pesticide may be about 4, 5, 6, 7, 8, 9, 10, 12, 13, 14, 15, 16, 17 or 18.

Non-limiting examples of fungal pesticides that may be used in the compositions disclosed herein are described in McCoy, C. W., Samson, R. A., and Coucias, D. G. "Entomogenous fungi. In "CRC Handbook of Natural Pesticides. Microbial Pesticides, Part A. Entomogenous Protozoa and Fungi." (C. M. Inoffo, ed.), (1988): Vol. 5, 151-236; Samson, R. A., Evans, H. C., and Latgé, J. P. "Atlas of Entomopathogenic Fungi." (Springer-Verlag, Berlin) (1988); and deFaria, M. R. and Wraight, S. P. "Mycoinsecticides and Mycoacaricides: A comprehensive list with worldwide coverage and international classification of formulation types." Biol. Control (2007), doi: 10.1016/j.biocontrol.2007.08.001.

In one embodiment, non-limiting examples fungal pesticides that may be used in the compositions disclosed herein include species of *Coelomycidium, Myiophagus, Coelemomyces, Lagenidium, Leptolegnia, Couchia, Sporodiniella, Conidiobolus, Entomophaga, Entomophthora, Erynia, Massospora, Meristacrum, Neozygites, Pandora, Zoophthora, Blastodendrion, Metschnikowia, Mycoderma, Ascophaera, Cordyceps, Torrubiella, Nectria, Hypocrella, Calonectria, Filariomyces, Hesperomyces, Trenomyces, Myriangium, Podonectria, Akanthomyces, Aschersonia, Aspergillus, Beauveria, Culicinomyces, Engyodontium, Fusarium, Gibellula, Hirsutella, Hymenostilbe, Isaria, Metarhizium, Nomuraea, Paecilomyces, Paraisaria, Pleurodesmospora, Polycephalomyces, Pseudogibellula, Sorosporella, Stillbella, Tetranacrium, Tilachlidium, Tolypocladium, Verticillium, Aegerita, Filobasidiella, Septobasidium, Uredinella*, and combinations thereof.

Non-limiting examples of particular species that may be useful as a fungal pesticide in the biopesticides described herein include *Trichoderma hamatum, Trichoderma hazarium, Alternaria cassiae, Fusarium lateritum, Fusarium solani, Lecanicillium lecanii, Aspergillus parasiticus, Verticillium lecanii, Metarhizium anisopliae*, and *Beauveria bassiana*. In an embodiment, the compositions disclosed herein may include any of the fungal pesticides provided above, including any combination thereof. In another embodiment, the fungal pesticide is stable so that the fungal pesticide retains a sufficient effective amount of activity when used. Methods for producing stabilized fungal organisms are known in the art. In one embodiment, the fungal pesticide is present in the composition in the form of a stable spore.

In one embodiment, the biopesticide comprises at least one fungal pesticide from the genus *Metarhizium* spp., such as, *Metarhizium anisopliae* (also may be referred to in the art as *Metarrhizium anisopliae, Metarhizium brunneum*, or "green muscadine"). In at least one embodiment, the fungal pesticide comprises the strain *Metarhizium anisopliae*. In another embodiment, the biopesticide comprises spores of the strain *Metarhizium anisopliae*.

In a particular embodiment, the biopesticide comprises at least one fungal pesticide comprising *Metarhizium anisopliae* strain F52 (also known as *Metarhizium*

*anisopliae* strain 52, *Metarhizium anisopliae* strain 7, *Metarhizium anisopliae* strain 43, *Metarhizium anisopliae* BIO-1020, TAE-001 and deposited as DSM 3884, DSM 3885, ATCC 90448, SD 170, and ARSEF 7711) (available from Novozymes Biologicals, Inc., USA). In still another particular embodiment, the biopesticide comprises at least one fungal pesticide comprising spores of *Metarhizium anisopliae* strain F52.

In yet another embodiment the biopesticide may further comprise at least one fungal pesticide from the genus *Beauveria* spp., such as, for example, *Beauveria bassiana*. In at least one embodiment, the fungal pesticide further comprises the strain *Beauveria bassiana*. In another embodiment, the biopesticide further comprises spores of the strain *Beauveria bassiana.*

In a particular embodiment, the biopesticide further comprises at least one fungal pesticide comprising *Beauveria bassiana* strain ATCC-74040. In another embodiment, the biopesticide further comprises at least one fungal pesticide comprising spores of *Beauveria bassiana* strain ATCC-74040. In another particular embodiment, the biopesticide further comprises at least one fungal pesticide comprising *Beauveria bassiana* strain ATCC-74250. In still another particular embodiment, the biopesticide further comprises at least one fungal pesticide comprising spores of *Beauveria bassiana* strain ATCC-74250. In yet another particular embodiment, the biopesticide further comprises at least one fungal pesticide comprising a mixture of *Beauveria bassiana* strain ATCC-74040 and *Beauveria bassiana* strain ATCC-74250. In still another embodiment, the biopesticide further comprises at least one fungal pesticide comprising a mixture of spores of *Beauveria bassiana* strain ATCC-74040 and *Beauveria bassiana* strain ATCC-74250.

In still yet another particular embodiment, the biopesticides described herein may comprise a combination of fungi. In one embodiment, the biopesticides may comprise two or more fungal pesticides that are different strains of the same species. In another embodiment, the biopesticide comprises at least two different fungal pesticides that are strains of different species. In an embodiment, the biopesticide comprises at least one fungal pesticide from the genus *Metarhizium* spp. and at least one fungal pesticide from the genus *Beauveria* spp. In another embodiment, the biopesticides comprise spores of *Metarhizium* spp. and *Beauveria* spp.

In a particular embodiment, the biopesticide comprises at least one fungal pesticide, wherein at least one fungal pesticide is a strain of *Metarhizium anisopliae* and at least one fungal pesticide is a strain of *Beauveria bassiana*. In another embodiment, the biopesticide comprises at least one fungal pesticide wherein the fungal pesticide comprises spores of *Metarhizium anisopliae* and *Beauveria bassiana.*

In a more particular embodiment, the biopesticide comprises at least one fungal pesticide, wherein at least one fungal pesticide is a strain of *Metarhizium anisopliae* F52 and at least one fungal pesticide is a strain of the strain *Beauveria bassiana* ATCC-74040. In yet another embodiment, the biopesticide comprises at least one fungal pesticide wherein the fungal pesticide comprises spores of the strain *Metarhizium anisopliae* F52 and the strain *Beauveria bassiana* ATCC-74040.

In still another particular embodiment, the biopesticide comprises at least one fungal pesticide, wherein at least one fungal pesticide is a strain of *Metarhizium anisopliae* F52 and at least one fungal pesticide is a strain of the strain *Beauveria bassiana* ATCC-74250. In yet another embodiment, the biopesticide comprises at least one fungal pesticide wherein the fungal pesticide comprises spores of the strain *Metarhizium anisopliae* F52 and the strain *Beauveria bassiana* ATCC-74250.

In still yet another particular embodiment, the biopesticide comprises at least one fungal pesticide, wherein at least one fungal pesticide is a strain of *Metarhizium anisopliae* F52, at least one fungal pesticide is a strain of the strain *Beauveria bassiana* ATCC-74040, and at least one fungal pesticide is a strain of the strain *Beauveria bassiana* ATCC-74250. In yet another embodiment, the biopesticide comprises at least one fungal pesticide wherein the fungal pesticide comprises spores of the strain *Metarhizium anisopliae* F52, the strain *Beauveria bassiana* ATCC-74040, and the strain *Beauveria bassiana* ATCC-74250.

The fungal pesticide may be produced in a liquid culture media or a solid culture media fermentation process. The media may have high carbon and nitrogen concentrations to facilitate higher yields. Not-limiting examples of suitable nitrogen sources include hydrolyzed casein, yeast extract, hydrolyzed soy protein, hydrolyzed cottonseed protein, and hydrolyzed corn gluten protein. Not-limiting examples of suitable carbon sources include carbohydrates, including glucose, fructose, and sucrose, and glycerol and/or grains such as rice or barley.

Fermentation processes may be conducted using conventional fermentation processes, such as, aerobic liquid-culture techniques, shake flask cultivation, and small-scale or large-scale fermentation (e.g., continuous, batch, fed-batch, solid state fermentation, etc.) in laboratory or industrial fermentors, and such processes are well known in the art. Notwithstanding the production process used to produce the fungal organism, it is envisioned that the fungal pesticide may be used as a pesticide directly from the culture medium (e.g., rice) or subject to purification and/or further processing steps (e.g., a drying process). In one embodiment, following fermentation, the fungal organism may be recovered using conventional techniques (e.g., by filtration, centrifugation, mechanical recovery (e.g., shaking the fungal organism from the culture medium), etc.). The fungal organism may alternatively be dried (e.g., air-drying, freeze drying, or spray drying to a low moisture level, and storing at a suitable temperature, e.g., room temperature).

Surfactant(s):

Surfactants are well known in the art and any combination of suitable surfactants or surfactant systems may be used for the biopesticide compositions described herein. Without being bound by theory, it is believed that the surfactants suitable for the biopesticides (i.e., compositions) described herein will modify the properties of the carrier to increase the dispersion and/or suspension of the biopesticide in aqueous solutions (i.e., stabilize oil-in-water emulsions when the biopesticide is diluted with water). It is further believed that by modifying the carrier to increase the dispersion and/or suspension of the biopesticide in an aqueous solution, that the biopesticide will be able to be delivered efficiently (e.g., through a sprayer) without actives adhering/sticking to the inner walls of the delivery device or clogging the delivery components (e.g., sprayer nozzles, sprayer tubing, etc.).

Suitable surfactants for the biopesticides disclosed herein will have minimal, if any negative effects, on the viability of the fungal pesticides.

In an embodiment, the biopesticide (i.e., the composition), may be formed of 1.00 wt. % to 50.00 wt. % of total surfactant. There may be minor variances when measuring the weight percentage of the total surfactant, and the biopesticide may be formed of about 1.00 wt. % to about 50.00 wt.

% of surfactant. In still another embodiment, the biopesticide may be formed of 1.00 wt. % to 40.00 wt. % of total surfactant. Again, there may be minor variances when measuring the weight percentage of the total surfactant, and the biopesticide may be formed of about 1.00 wt. % to about 40.00 wt. % of surfactant. In still yet another embodiment, the biopesticide is formed of 2.00 wt. % to 30.00 wt. % of total surfactant. Yet again, there may be minor variances when measuring the weight percentage of the total surfactant, and the biopesticide may be formed of about 2.00 wt. % to about 30.00 wt. % of surfactant. Therefore, in embodiments of the biopesticides disclosed herein, the total amount of surfactant may be as low as 1.00 wt. % and as high as 50.00 wt. % total surfactant (e.g., between 1.00 and 50.00 wt. % total surfactant). In other embodiments, the wt. % of total surfactant may be between about 29-31, 28-32, 27-33, 26-34, 25-35, 24-36, or 22-28.

In a particular embodiment, the biopesticide is formed of 7.50 wt. % of total surfactant. There may be minor variances when measuring the weight percentage of the total surfactant, and the biopesticide may be formed of about 7.50 wt. % surfactant. In another particular embodiment, the biopesticide is formed of 10.00 wt. % of total surfactant. There may be minor variances when measuring the weight percentage of the total surfactant, and the biopesticide may be formed of about 10.00 wt. % surfactant. In still another particular embodiment, the biopesticide is formed of 15.00 wt. % of total surfactant. There may be minor variances when measuring the weight percentage of the total surfactant, and the biopesticide may be formed of about 15.00 wt. % surfactant. In yet another particular embodiment, the biopesticide is formed of 20.00 wt. % of total surfactant. There may be minor variances when measuring the weight percentage of the total surfactant, and the biopesticide may be formed of about 20.00 wt. % surfactant. In still yet another particular embodiment, the biopesticide is formed of 25.00 wt. % of total surfactant. There may be minor variances when measuring the weight percentage of the total surfactant, and the biopesticide may be formed of about 25.00 wt. % surfactant. In yet still another particular embodiment, the biopesticide is formed of 27.75 wt. % of total surfactant. There may be minor variances when measuring the weight percentage of the total surfactant, and the biopesticide may be formed of about 27.75 wt. % surfactant. In another particular embodiment, the biopesticide is formed of 30.00 wt. % of total surfactant. There may be minor variances when measuring the weight percentage of the total surfactant, and the biopesticide may be formed of about 30.00 wt. % surfactant. In other embodiments, the wt. % of total surfactant may be about 21, 22, 23, 24, 26, 27, 28, 29, 31, 32, 33, 34, 35, 36, 37, 38, 39 or 40.

The following includes non-limiting examples of surfactants which may be suitable for use with the biopesticides described herein. The different kind of surfactants are chosen and comprised in certain ratios in order to obtain a biopesticide with certain properties (e.g., soluble in aqueous solution, not harmful to actives, minimal phytotoxic effects, reduced adherence/sticking to formulation applicators/devices, etc.).

Anionic Surfactants

The biopesticides described herein may comprise at least one or more anionic surfactants. The anionic surfactant(s) may be either water soluble anionic surfactants, water insoluble anionic surfactants, or a combination of water soluble anionic surfactants and water insoluble anionic surfactants.

Non-limiting examples of water soluble anionic surfactants include alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, alkyl carboxylates, or a combination thereof.

Commercially available anionic surfactants suitable for the biopestides described herein include Ninate 60E. In an embodiment, the biopesticide comprises Ninate 60E.

Nonionic Surfactants

The biopesticides described herein may comprise at least one or more nonionic surfactants. The nonionic surfactant(s) may be either water soluble nonionic surfactants, water insoluble nonionic surfactants, or a combination of water soluble nonionic surfactants and water insoluble nonionic surfactants.

Water Insoluble Nonionic Surfactants

Non-limiting examples of water insoluble nonionic surfactants include alkyl and aryl: glycerol ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty acid esters, sorbitol ethoxylate esters, or combinations thereof. Also included are EO/PO block copolymers (EO is ethylene oxide, PO is propylene oxide), EO polymers and copolymers, polyamines, and polyvinylpyrrolidones.

Commercially available water insoluble nonionic surfactants that may be suitable for the biopesticides described herein include Tomadol® 91-2.5, Tomadol® 23-1, Tomadol® 23-3, Span™ 20, Span™ 40, Span™ 60, Span™ 65, Span™ 80, Span™ 85, Arlatone® TV, Atlas® G-1086, Atlas® G-1096, Atlox® 1045A, Cirrasol® G-1086, Cirrasol® G-1096, and combinations thereof.

In one embodiment, the biopesticides described herein comprise at least one water insoluble nonionic surfactant. In another embodiment, the biopesticides described herein comprise at least one water insoluble nonionic surfactant selected from sorbitan fatty acid esters, sorbitol ethoxylate esters and combinations thereof. Non-limiting examples of sorbitan fatty acid esters that may be suitable for the biopesticides described herein include sorbitan monolaurates (e.g. Span™ 20), sorbitan monopalmitates (e.g. Span™ 40), sorbitan monostearates (e.g. Span™ 60), sorbitan tristearates (e.g. Span™ 65), sorbitan monooleates (e.g. Span™ 80), sorbitan trioleates (e.g. Span™ 85), and combinations thereof. Non-limiting examples of sorbitol ethoxylates esters that may be suitable for the biopesticides described herein include polyoxyethylene (40) sorbitol oleates (e.g., Arlatone® TV), polyoxyethylene (40) sorbitol hexaoleates (e.g., Atlas® G-1086, Cirrasol® G-1086), polyoxyethylene (50) sorbitol hexaoleates (e.g., Atlas® G-1096, Cirrasol® G-1096), polyoxyethylene (30) oleate-laurates (e.g., Atlox 1045A), and combinations thereof.

In another particular embodiment, the biopesticide comprises one or more sorbitan fatty esters selected from a sorbitan monolaurate, a sorbitan monopalmitate, a sorbitan monostearate, a sorbitan tristearate, a sorbitan monooleate, a sorbitan trioleate, and combinations thereof. In still another particular embodiment, the biopesticide comprises one or more sorbitol ethoxylates esters selected from a polyoxyethylene (40) sorbitol oleate, a polyoxyethylene (40) sorbitol hexaoleate, a polyoxyethylene (50) sorbitol hexaoleate, a polyoxyethylene (30) oleate-laurate, and combinations thereof. In yet another particular embodiment, the biopesticide comprises at least one sorbitan fatty acid ester, wherein the sorbitan fatty ester is selected from a sorbitan monolaurate, a sorbitan monopalmitate, a sorbitan monostearate, a sorbitan tristearate, a sorbitan monooleate, a sorbitan trioleata, and combinations thereof, and a sorbitol ethoxylate ester, wherein the sorbitol ethoxylates ester is selected from a polyoxyethylene (40) sorbitol oleate, a polyoxyethylene (40) sorbitol hexaoleate, a polyoxyethylene (50) sorbitol hexaoleate, a polyoxyethylene (30) oleate-laurate, and combinations thereof.

In another embodiment, the biopesticide comprises a sorbitan monostearate. In still another embodiment, the biopesticide comprises a sorbitan monooleate. In still yet another embodiment, the biopesticide comprises a polyoxyethylene (40) sorbitol hexaoleate. In a particular embodiment, the biopesticide comprises a sorbitan monostearate, a sorbitan monooleate, a polyoxyethylene (40) sorbitol hexaoleate, and combinations thereof. In another particular embodiment, the biopesticide comprises a sorbitan monostearate, a sorbitan monooleate, and combinations thereof. In yet another particular embodiment, the biopesticide comprises a sorbitan monostearate, a polyoxyethylene (40) sorbitol hexaoleate, and combinations thereof. In still another particular embodiment, the biopesticide comprises a sorbitan monooleate, a polyoxyethylene (40) sorbitol hexaoleate, and combinations thereof.

In a particular embodiment, the biopesticide comprises Span™ 60. In another particular embodiment, the biopesticide comprises Span™ 80. In still another particular embodiment, the biopesticide comprises a mixture of Span™ 60 and Span™ 80. In yet another particular embodiment, the biopesticide comprises Cirrasol® G-1086. In yet another particular embodiment, the biopesticide comprises Atlas® G-1086. In another particular embodiment, the biopesticide comprises a mixture of Cirrasol® G-1086 and Atlas® G-1086. In still yet another particular embodiment, the biopesticide comprises a mixture of Cirrasol® G-1086 and Span™ 60. In another particular embodiment, the biopesticide comprises a mixture of Cirrasol® G-1086 and Span™ 80. In still yet another particular embodiment, the biopesticide comprises a mixture of Atlas® G-1086 and Span™ 60. In yet another particular embodiment, the biopesticide comprises a mixture of Atlas® G-1086 and Span™ 80. In another particular embodiment, the biopesticide comprises a mixture of Cirrasol® G-1086, Span™ 60, and Span™ 80. In still another particular embodiment, the biopesticide comprises a mixture of Atlas® G-1086, Span™ 60, and Span™ 80. In still yet another particular embodiment, the biopesticide comprises a mixture of Atlas® G-1086, Cirrasol® G-1086, and Span™ 60. In yet another particular embodiment, the biopesticide comprises a mixture of Atlas® G-1086, Cirrasol® G-1086, and Span™ 80. In yet still another particular embodiment, the biopesticide comprises a mixture of Atlas® G-1086, Cirrasol® G-1086, Span™ 60, and Span™ 80.

In a particular embodiment, the biopesticide comprises at least one sorbitan fatty acid ester and at least sorbitol ethoxylate ester wherein the ratio of sorbitan fatty acid ester to sorbitol ethoxylate ester is between 1:100 to 100:1. In a more particular embodiment, the ratio of sorbitan fatty acid ester to sorbitol ethoxylate ester is between 1:90 to 90:1. In another embodiment, the ratio of sorbitan fatty acid ester to sorbitol ethoxylate ester is between 1:80 to 80:1. In still another embodiment, the ratio of sorbitan fatty acid ester to sorbitol ethoxylate ester is between 1:70 to 70:1. In still yet another embodiment, the ratio of sorbitan fatty acid ester to sorbitol ethoxylate ester is between 1:60 to 60:1. In another embodiment, the ratio of sorbitan fatty acid ester to sorbitol ethoxylate ester is between 1:50 to 50:1. In still another embodiment, the ratio of sorbitan fatty acid ester to sorbitol ethoxylate ester is between 1:40 to 40:1. In yet another embodiment, the ratio of sorbitan fatty acid ester to sorbitol ethoxylate ester is between 1:30 to 30:1. In still yet another embodiment, the ratio of sorbitan fatty acid ester to sorbitol ethoxylate ester is between 1:20 to 20:1. In another embodiment, the ratio of sorbitan fatty acid ester to sorbitol ethoxylate ester is between 1:10 to 10:1. In still another embodiment, the ratio of sorbitan fatty acid ester to sorbitol ethoxylate ester is 1:1.

In a particular embodiment, the ratio of sorbitan fatty acid ester to sorbitol ethoxylate ester is 5:95 or 95:5. In another particular embodiment, the ratio of sorbitan fatty acid ester to sorbitol ethoxylate ester is 10:90 or 90:10. In still another particular embodiment, the ratio of sorbitan fatty acid ester to sorbitol ethoxylate ester is 7.5:92.5 or 92.5:7.5. In still yet another a particular embodiment, the ratio of sorbitan fatty acid ester to sorbitol ethoxylate ester is 15:85 or 85:15.

In a particular embodiment, the biopesticide comprises at least one sorbitan monooleate and at least one polyoxyethylene (40) sorbitol hexaoleate wherein the ratio of sorbitan monooleate to polyoxyethylene (40) sorbitol hexaoleate is between 1:100 to 100:1. In a more particular embodiment, the ratio of sorbitan monooleate to polyoxyethylene (40) sorbitol hexaoleate is between 1:90 to 90:1. In another embodiment, the ratio of sorbitan monooleate to polyoxyethylene (40) sorbitol hexaoleate is between 1:80 to 80:1. In still another embodiment, the ratio of sorbitan monooleate to polyoxyethylene (40) sorbitol hexaoleate is between 1:70 to 70:1. In still yet another embodiment, the ratio of sorbitan monooleate to polyoxyethylene (40) sorbitol hexaoleate is between 1:60 to 60:1. In another embodiment, the ratio of sorbitan monooleate to polyoxyethylene (40) sorbitol hexaoleate is between 1:50 to 50:1. In still another embodiment, the ratio of sorbitan monooleate to polyoxyethylene (40) sorbitol hexaoleate is between 1:40 to 40:1. In yet another embodiment, the ratio of sorbitan monooleate to polyoxyethylene (40) sorbitol hexaoleate is between 1:30 to 30:1. In still yet another embodiment, the ratio of sorbitan monooleate to polyoxyethylene (40) sorbitol hexaoleate is between 1:20 to 20:1. In another embodiment, the ratio of sorbitan monooleate to polyoxyethylene (40) sorbitol hexaoleate is between 1:10 to 10:1. In still another embodiment, the ratio of sorbitan monooleate to polyoxyethylene (40) sorbitol hexaoleate is 1:1.

In a particular embodiment, the ratio of sorbitan monooleate to polyoxyethylene (40) sorbitol hexaoleate is 5:95 or 95:5. In another particular embodiment, the ratio of sorbitan monooleate to polyoxyethylene (40) sorbitol hexaoleate is 10:90 or 90:10. In still another particular embodiment, the ratio of sorbitan monooleate to polyoxyethylene (40) sorbitol hexaoleate is 7.5:92.5 or 92.5:7.5. In still yet another particular embodiment, the ratio of sorbitan monooleate to polyoxyethylene (40) sorbitol hexaoleate is 15:85 or 85:15.

In particular embodiments, the ratio of sorbitan monooleate or sorbitan monooleate, to polyoxyethylene (40) sorbitol hexaoleate may be 0.01, 0.02, 0.03, 0.04, 0.05, 0.06, 0.07, 0.08, 0.09, 0.10, 0.11. 0.12. 0.13, 0.14, 0.15, 0.20, 0.25, 0.30, and the like.

In a particular embodiment, the biopesticide comprises at least one Span™ 80 and at least one Cirrasol® G-1086 wherein the ratio of Span™ 80 to Cirrasol® G-1086 is between 1:100 to 100:1. In a more particular embodiment, the ratio of Span™ 80 to Cirrasol® G-1086 is between 1:90 to 90:1. In another embodiment, the ratio of Span™ 80 to Cirrasol® G-1086 is between 1:80 to 80:1. In still another embodiment, the ratio of Span™ 80 to Cirrasol® G-1086 is between 1:70 to 70:1. In still yet another embodiment, the ratio of Span™ 80 to Cirrasol® G-1086 is between 1:60 to 60:1. In another embodiment, the ratio of Span™ 80 to Cirrasol® G-1086 is between 1:50 to 50:1. In still another embodiment, the ratio of Span™ 80 to Cirrasol® G-1086 is between 1:40 to 40:1. In yet another embodiment, the ratio of Span™ 80 to Cirrasol® G-1086 is between 1:30 to 30:1. In still yet another embodiment, the ratio of Span™ 80 to Cirrasol® G-1086 is between 1:20 to 20:1. In another embodiment, the ratio of Span™ 80 to Cirrasol® G-1086 is between 1:10 to 10:1. In still another embodiment, the ratio of Span™ 80 to Cirrasol® G-1086 is 1:1.

In a particular embodiment, the ratio of Span™ 80 to Cirrasol® G-1086 is 5:95 or 95:5. In another particular embodiment, the ratio of Span™ 80 to Cirrasol® G-1086 is 10:90 or 90:10. In still another particular embodiment, the ratio of Span™ 80 to Cirrasol® G-1086 is 7.5:92.5 or 92.5:7.5. In still yet another particular embodiment, the ratio of Span™ 80 to Cirrasol® G-1086 is 15:85 or 85:15.

In particular embodiments, the ratio of Span™ 60 or Span™ 80, to Cirrasol® G-1086 may be 0.01, 0.02, 0.05, 0.10, 0.15, 0.20, 0.25, 0.30, 0.35, 0.40, 0.45 and the like.

Water Soluble Nonionic Surfactants

Non-limiting examples of water soluble nonionic surfactants include sorbitan fatty acid alcohol ethoxylates and sorbitan fatty acid ester ethoxylates. In one embodiment, the biopesticide comprises at least one water soluble nonionic surfactant that is a linear primary, or secondary or branched alcohol ethoxylate having the formula: $RO(CH_2CH_2O)_nH$, wherein R is the hydrocarbon chain length and n is the average number of moles of ethylene oxide. In an embodiment, R can be a linear primary, or secondary, or branched alcohol ethoxylates having a hydrocarbon chain length in the range from C9 to C16 and n ranges from 6 to 13. In another embodiment the biopesticide comprises at least one alcohol ethoxylate where R is linear C9-C11 hydrocarbon chain length, and n is 6. In still another embodiment, when the biopesticides described herein comprise more than one water soluble surfactant, the water soluble surfactants are of substantially the same carbon chain length.

Commercially available water soluble nonionic surfactants that may be suitable for the biopesticides described herein include Tomadol® 9-11, Tomadol® 23-7, Tomadol® 91-6, Tween® 20, Tween® 21, Tween® 40, Tween® 60, Tween® 80, Surfonic L24-4, and combinations thereof.

In one embodiment, the biopesticides described herein comprise at least one water soluble nonionic surfactant selected from the group consisting of Tomadol® 9-11, Tomadol® 23-7, Tomadol® 91-6, and combinations thereof.

In a particular embodiment, the biopesticides described herein comprise at least one sorbitan fatty acid ester ethoxylate selected from the group consisting of Tween® 20, Tween® 21, Tween® 40, Tween® 60, Tween® 80, Surfonic L24-4, and combinations thereof.

In still another embodiment, the biopesticides described herein comprise at least one alcohol ethoxylate, at least one sorbitan fatty acid ester ethoxylate, or a combination thereof. In still another embodiment, the biopesticides described herein comprise at least one water soluble nonionic surfactant selected from the group consisting of Tomadol® 9-11, Tomadol® 23-7, Tomadol® 91-6, Tween® 20, Tween® 21, Tween® 40, Tween® 60, Tween® 80, Surfonic L24-4, and combinations thereof.

In a particular embodiment, the biopesticide comprises Surfonic L24-4.

Combination of Nonionic Surfactants

In one embodiment, the biopesticides described herein comprise one or more nonionic surfactants. In another embodiment, the biopesticides comprise one or more water insoluble nonionic surfactants. In still another embodiment, the biopesticides comprise one or more water insoluble nonionic surfactants and one or more water soluble nonionic surfactants.

Other Surfactants

In another embodiment, the biopesticides described herein may also comprise silicone-based antifoams used as surfactants in silicone-based and mineral-oil based antifoams.

In another embodiment, the biopesticides described herein may also comprise alkali metal salts of fatty acids (e.g., water soluble alkali metal salts of fatty acids and/or water insoluble alkali metal salts of fatty acids) of greater than 10 carbons in length. In an embodiment, biopesticides comprising alkali metal salts of fatty acids comprise carbon chains greater than or equal to 18 carbons in length. In still another embodiment, biopesticides comprising alkali metal salts of fatty acids comprise carbon chains greater than or equal to 20 carbons in length.

Optional Ingredients:

The biopesticides (i.e., the compositions described herein) may further comprise one or more optional ingredients that are physically and/or chemically compatible with the biopesticides embodied herein. Non-limiting optional ingredients include anti-settling agents, agriculturally beneficial ingredients (e.g., enzymes, beneficial plant signal molecules, beneficial microorganisms, insecticides, fungicides, nematicides, nutrients, etc.), insect growth regulators, electrostatic carriers, preservatives, fillers, pH adjusting agents, stabilizers, builders, buffers, antioxidants, water absorbing agents, foams, humectants, wetting agents UV protectants, solvents, nutritive additives, and combinations thereof. Such ingredients are known to those skilled in the art.

Anti-Settling Agents

In at least one embodiment, the biopesticides (i.e., compositions described herein) may optionally comprise one or more anti-settling agents. Alternatively, the one or more anti-settling agents may be applied either simultaneously or applied sequentially, with the biopesticides disclosed herein. The one or more anti-settling agents may comprise any agent capable of maintaining insoluble particles (i.e., fungal pesticide spores) uniformly suspended in liquid solution (i.e., prevent insoluble from settling).

In embodiments, the biopesticide, may be formed of 0.01 wt. % to 10.00 wt. % of anti-settling agent. There may be minor variances when measuring the weight percentage of the anti-settling agent and the biopesticide may be formed of about 0.01 wt. % to about 10.00 wt. % of anti-settling agent. In still another embodiment, the biopesticide may be formed of 0.01 wt. % to 5.00 wt. % of anti-settling agent. Again, there may be minor variances when measuring the weight percentage of the anti-settling agent and the biopesticide may be formed of about 0.01 wt. % to about 5.00 wt. % of anti-settling agent. In still yet another embodiment, the biopesticide is formed of 0.01 wt. % to 2.00 wt. % of anti-settling agent. Yet again, there may be minor variances when measuring the weight percentage of the anti-settling agent and the biopesticide may be formed of about 0.01 wt. % to about 2.00 wt. % of anti-settling agent. Therefore, in embodiments of the biopesticides disclosed herein, the total amount of anti-settling agent may be as low as 1.00 wt. % and as high as 50.00 wt. % anti-settling agent (e.g., between 1.00 and 50.00 wt. % anti-settling agent).

In a particular embodiment, the biopesticide is formed of 0.25 wt. % of anti-settling agent. There may be minor variances when measuring the weight percentage of the anti-settling agent and the biopesticide may be formed of about 0.25 wt. % anti-settling agent. In a more particular embodiment, the biopesticide is formed of 0.50 wt. % of anti-settling agent. There may be minor variances when measuring the weight percentage of the anti-settling agent and the biopesticide may be formed of about 0.50 wt. % anti-settling agent. In another particular embodiment, the biopesticide is formed of 1.00 wt. % of anti-settling agent. There may be minor variances when measuring the weight percentage of the anti-settling agent and the biopesticide may be formed of about 1.00 wt. % anti-settling agent. In yet another particular embodiment, the biopesticide is formed of 3.00 wt. % of anti-settling agent. There may be minor variances when measuring the weight percentage of the anti-settling agent and the biopesticide may be formed of about 3.00 wt. % anti-settling agent. In still yet another particular embodiment, the biopesticide is formed of 5.00 wt. % of anti-settling agent. There may be minor variances when measuring the weight percentage of the anti-settling agent and the biopesticide may be formed of about 5.00 wt. % anti-settling agent. In other embodiments, the wt. % of anti-settling agent may be about 2 or 4.

Non-limiting examples of anti-settling agents that may be suitable for the biopesticides described herein polyvinyl acetate, polyvinyl alcohols with different degrees of hydrolysis, polyvinylpyrrolidones, polyacrylates, acrylate-, polyol- or polyester-based paint system binders which are soluble or dispersible in water, moreover copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, ot-methylstyrene or p-methylstyrene, further vinyl halides such as vinyl chloride and vinylidene chloride, additionally vinyl esters such as vinyl acetate, vinyl propionate or vinyl stearate, moreover vinyl methyl ketone or esters of acrylic acid or methacrylic acid with monohydric alcohols or polyols such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, furthermore diethyl esters or monoesters of unsaturated dicarboxylic acids, furthermore (meth)acrylamido-N-methylol methyl ether, amides or nitriles such as acrylamide, methacrylamide, N-methylol(meth)acrylamide, acrylonitrile, methacrylonitrile, and also N-substituted maleiraides and ethers such as vinyl butyl ether, vinyl isobutyl ether or vinyl phenyl ether, and combinations thereof. In another embodiment, the gelling agents which may be used include hydrophobically-modified clays (e.g., sodium montmorillonite where exchangeable sodium ions are replaced with organic cationic molecules, such as, alkylamines), surface modified silicas, fumed silicas (e.g., untreated, or surface-modified), and combinations thereof. Commercially available untreated fumed silicas include CAB-O-SIL® M-5, CAB-O-SIL® M-7D, CAB-O-SIL® MS-75D PDS, CAB-O-SIL® S-17D, CAB-O-SIL® EH-5, CAB-O-SIL® H-300, CAB-O-SIL® H-5, CAB-O-SIL® LM-150, CAB-O-SIL® MS-35, etc. (available from Cabot Corporation, Tuscola, Ill.). Surface-modified fumed silicas include, for example, fumed silicas surface-modified with hexamethyldisilazane, dimethyldichlorosilane (DiMeDi), polydimethylsiloxane, etc. Non-limiting examples of commercially available surface-modified fumed silicas include CAB-O-SIL® TS-530, CAB-O-SIL® TS-530D, CAB-O-SIL® TS-610, CAB-O-SIL® TS-622, CAB-O-SIL® TS-720, etc. (available from Cabot Corporation, Tuscola, Ill.).

In a particular embodiment, the biopesticide comprises fumed silica. In a more particular embodiment, the biopesticide comprises fumed silica, wherein the weight percentage of the biopesticide is 5.00 wt. % fumed silica. In another particular embodiment, the biopesticide comprises fumed silica, wherein the weight percentage of the biopesticide is 3.00 wt. % fumed silica. In still another particular embodiment, the biopesticide comprises fumed silica, wherein the weight percentage of the biopesticide is 1.00 wt. % fumed silica. In a more particular embodiment, the biopesticide comprises Cab-O-Sil® M-5, wherein the weight percentage of the biopesticide is 5.00 wt. % Cab-O-Sil® M-5. In still a more particular embodiment, the biopesticide comprises Cab-O-Sil® M-5, wherein the weight percentage of the biopesticide is 3.00 wt. % Cab-O-Sil® M-5. In still yet a more particular embodiment, the biopesticide comprises Cab-O-Sil® M-5, wherein the weight percentage of the biopesticide is 1.00 wt. % Cab-O-Sil® M-5.

Agriculturally Beneficial Ingredients

The biopesticides (i.e. compositions described herein) may optionally include one or more agriculturally beneficial ingredients. Non-limiting examples of agriculturally beneficial ingredients include one or more biologically active ingredients, nutrients, biostimulants, herbicides, fungicides, insecticides, or combinations thereof.

Biologically Active Ingredient(s):

Non-limiting examples of biologically active ingredients include enzymes, plant signal molecules (e.g., lipo-chitooligosaccharides (LCO), chitooligosaccharides (CO), chitinous compounds, jasmonic acid or derivatives thereof, linoleic acid or derivatives thereof, linolenic acid or derivatives thereof, karrikins, etc.) and beneficial microorganisms (e.g., *Rhizobium* spp., *Bradyrhizobium* spp., *Sinorhizobium* spp., *Azorhizobium* spp., *Glomus* spp., *Gigaspora* spp., *Hymenoscyphous* spp., *Oidiodendron* spp., *Laccaria* spp., *Pisolithus* spp., *Rhizopogon* spp., *Scleroderma* spp., *Rhizoctonia* spp., *Acinetobacter* spp., *Arthrobacter* spp., *Arthrobotrys* spp., *Aspergillus* spp., *Azospirillum* spp, *Bacillus* spp, *Burkholderia* spp., *Candida* spp., *Chryseomonas* spp., *Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., etc.).

Enzymes:

In at least one embodiment, the biopesticides (i.e., compositions described herein) may optionally comprise one or more enzymes. Alternatively, the one or more enzymes may be applied either simultaneously or applied sequentially, with the biopesticides disclosed herein. The biopesticides described herein may comprise at least one cuticle degrading enzymes. Cuticle degrading enzymes are well known in the art, and include both naturally occurring (wild-type) enzymes and variant (modified by humans) enzymes. Non-limiting examples of cuticle degrading enzymes include proteases, peptidases, chitinases, chitosanase, cutinases, and lipases. In an embodiment, the biopesticides optionally comprises at least one cuticle degrading enzyme selected from the group consisting of protease, peptidase, chitinase, chitosanase, lipase, cutinase, and any combination thereof. In another embodiment the at least one cuticle degrading enzyme is a protease. In another embodiment the at least one cuticle degrading enzyme is a chitinase. In yet another embodiment the at least one cuticle degrading enzyme is a lipase. In still another embodiment the at least one cuticle degrading enzyme is a cutinase.

In at least one embodiment the biopesticides described herein comprise a combination of at least two cuticle degrading enzymes (e.g., two cuticle degrading enzymes, three cuticle degrading enzymes, four cuticle degrading enzymes, five cuticle degrading enzymes, etc.). In one embodiment, the biopesticides described herein comprise a combination of at least two different types of enzymes (e.g., a protease and chitinase). In yet another embodiment, the biopesticides described herein comprise a combination of at least two of the same type of enzyme (e.g., at least two different proteases, etc.). In still another embodiment, the biopesticides described herein comprise a combination of at least three cuticle degrading enzymes (e.g., a protease, a chitinase, a lipase, etc.).

Enzymes described herein may possess one or more cuticle degrading activities. The cuticle degrading enzyme may be obtained from any suitable source. In embodiments, the cuticle degrading enzyme may be obtained from a microorganism (e.g., a bacterial source or a fungal source). In another embodiment, the cuticle degrading enzyme is the protease described in WO 89/06279. Commercial proteases may also be used, such as, e.g. the product SAVINASE (available from Novozymes A/S).

Enzymes described herein may also be isolated from an entomopathogenic fungus or an acaripathogenic fungus.

Non-limiting examples of cuticle degrading enzymes are described in Bagga, S., et al. "Reconstructing the diversification of subtilisins in the pathogenic fungus *Metarhizium anisopliae*." Gene 324 (2004): 159-69; Bidochka, M. J. and M. J. Melzer. "Genetic polymorphisms in three subtilisin-like protease isoforms (Pr1A, Pr1B, and Pr1C) from *Metarhizium* strains." Canadian Journal of Microbiology 46.12 (2000): 1138-44; Braga, G. U. L., R. Vencovsky, and C. L. Messias. "Estimates of genetic parameters related to chitinase production by the entomopathogenic fungus *Metarhizium anisopliae*." Genetics and Molecular Biology 21.2 (1998): 171-77; Clarkson, J. M. "Molecular biology of fungi for the control of insects." (1996): 123-35; Cole, S. C. J., A. K. Charnley, and R. M. Cooper. "Purification and partial characterization of a novel trypsin-like cysteine protease from *Metarhizium-anisopliae*." FEMS Microbiology Letters 113.2 (1993): 189-96; Da Silva, M. V., et al. "Cuticle-induced endo/exoacting chitinase CHIT30 from *Metarhizium anisopliae* is encoded by an ortholog of the chi3 gene." Research in Microbiology 156.3 (2005): 382-92; Dhar & Kaur, "Production of cuticle-degrading proteases by *Beauveria bassiana* and their induction in different media," African Journal of Biochemistry Research, Vol. 4(3), 65-72 (2010); Fang, W. G., et al. "Expressing a fusion protein with protease and chitinase activities increases the virulence of the insect pathogen *Beauveria bassiana*." Journal of Invertebrate Pathology 102.2 (2009): 155-59; Freimoser, F. M., et al. "Expressed sequence tag (EST) analysis of two subspecies of *Metarhizium anisopliae* reveals a plethora of secreted proteins with potential activity in insect hosts." Microbiology-Sgm 149 (2003): 239-47; Gimenez-Pecci, MdIP, et al. "Characterization of mycoviruses and analyses of chitinase secretion in the biocontrol fungus *Metarhizium anisopliae*." Current Microbiology 45.5 (2002): 334-39; Hu, G. and R. J. S. Leger. "A phylogenomic approach to reconstructing the diversification of serine proteases in fungi." Journal of Evolutionary Biology 17.6 (2004): 1204-14; Hutwimmer, S., et al. "Algorithm-based design of synthetic growth media stimulating virulence properties of *Metarhizium anisopliae* conidia." Journal of Applied Microbiology 105.6 (2008): 2026-34; Joshi, L., R. S. S. Leger, and D. W. Roberts. "Isolation of a cDNA encoding a novel subtilisin-like protease (Pr1B) from the entomopathogenic fungus, *Metarhizium anisopliae* using differential display-RT-PCR." Gene (Amsterdam) 197.1-2 (1997): 1-8; Kim, H. K., et al. "Gene structure and expression of the gene from *Beauveria bassiana* encoding bassiasin I, an insect cuticle-degrading serine protease." Biotechnology Letters 21.9 (1999): 777-83; Kim, J. S. "A novel biopesticide production: Attagel-mediated precipitation of chitinase from *Beauveria bassiana* SFB-205 supernatant for thermotolerance." Applied Microbiology and Biotechnology 87.5 (2010): 1639-48; "Relation of aphicidal activity with cuticular degradation by *Beauveria bassiana* SFB-205 supernatant incorporated with polyoxyethylene-(3)-isotridecyl ether." Journal of Microbiology and Biotechnology 20.3 (2010): 506-09; Kim, J. S., et al. "Influence of two FPLC fractions from *Beauveria bassiana* SFB-205 supernatant on the insecticidal activity against cotton aphid." Biocontrol Science and Technology 20.1 (2010): 77-81; Kim, J. S., et al. "Correlation of the aphicidal activity of *Beauveria bassiana* SFB-205 supernatant with enzymes." Fungal Biology 114.1 (2010): 120-28; Ko, H. J., et al. "Optimal production of protease from entomopathogenic fungus *Beauveria bassiana*." Agricultural Chemistry and Biotechnology 39.6 (1996): 449-54; Ko, H. J., et al. "Purification and characterization of protease from entomopathogenic fungus *Beauveria bassiana*." Agricultural Chemistry and Biotechnology 40.5 (1997): 388-94; Leal, S. C. M., et al. "Amplification and restriction endonuclease digestion of the Pr1 gene for the detection and characterization of *Metarhizium* strains." Mycological Research 101.3 (1997): 257-65; Liang et al., "The crystal structures of two cuticle-degrading proteases from nematophagous fungi and their contribution to infection against nematodes," The FASEB Journal, Vol. 24, 1391-1400, May 2010; Manalil, N. S., et al. "Comparative analysis of the *Metarhizium anisopliae* secretome in response to exposure to the greyback cane grub and grub cuticles." Fungal Biology 114.8 (2010): 637-45; Mohanty, S. S., K. Raghavendra, and A. P. Dash. "Induction of chymoelastase (Pr1) of *Metarhizium anisopliae* and its role in causing mortality to mosquito larvae." World Journal of Microbiology and Biotechnology 24.10 (2008): 2283-88; Mustafa, U. and G. Kaur. "Extracellular Enzyme Production in *Metarhizium anisopliae* Isolates." Folia Microbiologica 54.6 (2009): 499-504; Nahar, P., V. Ghormade, and M. V. Deshpande. "The extracellular constitutive production of chitin deacetylase in *Metarhizium anisopliae*: possible edge to entomopathogenic fungi in the biological control of insect pests." Journal of Invertebrate Pathology 85.2 (2004): 80-88; Ortiz-Urquiza, A., et al. "Effects of cultural conditions on fungal biomass, blastospore yields and toxicity of fungal secreted proteins in batch cultures of *Metarhizium anisopliae* (Ascomycota: Hypocreales)." Pest Management Science 66.7 (2010): 725-35; Paterson, I. C., et al. "Regulation of production of a trypsin-like protease by the insect pathogenic fungus *Metarhizium-anisopliae*." FEMS Microbiology Letters 109.2-3 (1993): 323-27; "Specific induction of a cuticle-degrading protease of the insect pathogenic fungus *Metarhizium-anisopliae*." Microbiology-Uk 140. Part 1 (1994): 185-89; "Partial characterization of specific inducers of a cuticle-degrading protease from the insect pathogenic fungus *Metarhizium-anisopliae*." Microbiology-Uk 140. Part 11 (1994): 3153-59; Pinto, F. G., et al. "Genetic variation in the cuticle-degrading protease activity of the entomopathogen *Metarhizium flavoviride*." Genetics and Molecular Biology 25.2 (2002): 231-34; Qazi, S. S. and G. G. Khachatourians. "Hydrated conidia of *Metarhizium anisopliae* release a family of metalloproteases." Journal of Invertebrate Pathology 95.1 (2007): 48-59; Rangel, D. E. N., D. G. Alston, and D. W. Roberts. "Effects of physical and nutritional stress conditions during mycelial growth on conidial germination speed, adhesion to host cuticle, and virulence of *Metarhizium anisopliae*, an entomopathogenic fungus." Mycological Research 112 (2008): 1355-61; Rodriguez, C. ML and B. C E Gongora. "Transformation of *Beauveria bassiana* Bb9205 with pr1A, pr1J, and ste1 genes of *Metarhizium anisopliae* and evaluation of the pathogenicity on the coffee berry borer." REVISTA COLOMBIANA DE ENTOMOLOGIA 31.1 (2005): 51-58; Santi, L., et al. "Differential immunoproteomics enables identification of *Metarhizium anisopliae* proteins related to *Rhipicephalus microplus* infection." Research in Microbiology 160.10 (2009): 824-28; Santi, L., et al. "*Metarhizium anisopliae* host-pathogen interaction: differential immunoproteomics reveals proteins involved in the infection process of arthropods." Fungal Biology 114.4 (2010): 312-19; Sasaki, S. D., et al. "BmSI-7, a novel subtilisin inhibitor from *Boophilus microplus*, with activity toward Pr1 proteases from the fungus *Metarhizium anisopliae*." Experimental Parasitology 118.2 (2008): 214-20; Screen, S. E., G. Hu, and R. J. Leger. "Transformants of *Metarhizium anisopliae* sf. *anisopliae* overexpressing chitinase from *Metarhizium anisopliae* sf. *acridum* show early induction of native chitinase but are not altered in pathogenicity to *Manduca sexta*." Journal of Invertebrate Pathology 78.4 (2001): 260-66; Segers, R., et al. "The subtilisins of the invertebrate mycopathogens *Verticillium chlamydosporium* and *Metarhizium anisopliae* are serologically and functionally related." FEMS Microbiology Letters 126.3 (1995): 227-31; Shah, F. A., C. S. Wang, and T. M. Butt. "Nutrition influences growth and virulence of the insect-pathogenic fungus *Metarhizium anisopliae*." FEMS Microbiology Letters 251.2 (2005): 259-66; Small, C. L. and M. J. Bidochka. "Up-regulation of Pr1, a subtilisin-like protease, during conidiation in the insect pathogen *Metarhizium anisopliae*." Mycological Research 109 (2005): 307-13; Smithson, S. L., et al. "Cloning and characterization of a gene encoding a cuticle-degrading protease from the insect pathogenic fungus *Metarhizium anisopliae*." Gene (Amsterdam) 166.1 (1995): 161-65; St Leger, R. J. "The role of cuticle-degrading proteases in fungal pathogenesis of insects." Canadian Journal of Botany 73.SUPPL. 1 SECT. E-H (1995): S1119-S1125; St Leger, R. J., M. J. Bidochka, and D. W. Roberts. "Characterization of a novel carboxypeptidase produced by the entomopathogenic fungus *Metarhizium anisopliae*." Archives of biochemistry and biophysics 314.2 (1994): 392-98; "Germination triggers of *Metarhizium anisopliae* conidia are related to host species." Microbiology (Reading) 140.7 (1994): 1651-60; St Leger, R. J., R. M. Cooper, and A. K. Charnley. "Distribution of chymoelastases and trypsin-like enzymes in five species of entomopathogenic deuteromycetes." Archives of biochemistry and biophysics 258.1 (1987): 123-31; St Leger, R. J., L. Joshi, and D. W. Roberts. "Adaptation of proteases and carbohydrates of saprophytic, phytopathogenic and entomopathogenic fungi to the requirements of their ecological niches." Microbiology (Reading, England) 143 (Pt 6) (1997): 1983-92; St Leger, R. J., J. O. Nelson, and S. E. Screen. "The entomopathogenic fungus *Metarhizium anisopliae* alters ambient pH, allowing extracellular protease production and activity." Microbiology-Uk 145 (1999): 2691-99; St Leger, R. J. and D. W. Roberts. "Engineering improved mycoinsecticides." Trends in Biotechnology 15.3 (1997): 83-85; St Leger, R. J., M. J. Bidochka, and D. W. Roberts. "Isoforms of the cuticle-degrading pr1 proteinase and production of a metalloproteinase by *Metarhizium-anisopliae*." Archives of biochemistry and biophysics 313.1 (1994): 1-7; St Leger, R. J., R. M. Cooper, and A. K. Charnley. "Analysis of aminopeptidase and dipeptidylpeptidase iv from the entomopathogenic fungus *Metarhizium-anisopliae*." Journal of General Microbiology 139. Part 2 (1993): 237-43; St Leger, R. J., et al. "Characterization and ultrastructural-localization of chitinases from *Metarhizium-anisopliae*, m-*flavoviride*, and *Beauveria-bassiana* during fungal invasion of host (manduca-sexta) cuticle." Applied and Environmental Microbiology 62.3 (1996): 907-12; St Leger, R. J., L. Joshi, and D. Roberts. "Ambient pH is a major determinant in the expression of cuticle-degrading enzymes and hydrophobin by *Metarhizium-anisopliae*." Applied and Environmental Microbiology 64.2 (1998): 709-13; St Leger, R. J., R. C. Staples, and D. W. Roberts. "Entomopathogenic isolates of *Metarhizium-anisopliae*, *Beauveria-bassiana*, and *Aspergillus-flavus* produce multiple extracellular chitinase isozymes." Journal of Invertebrate Pathology 61.1 (1993): 81-84; St. Leger et al., "Production of Cuticle-degrading Enzymes by the Entomopathogen *Metarhizium anisopliae* during Infection of Cuticles from *Calliphora vomitoria* and *Manduca sexta*," Journal of General Microbiology, 133, 1371-1382 (1987); St. Leger et al., "Cuticle-degrading Enzyme of Entomopathogenic Fungi: Regulation of Production of Chitonolytic Enzymes," General Microbiology, 132, 1509-1517 (1987); St. Leger et al., "Cuticle-Degrading Enzymes of Entomopathogenic Fungi," Synthesis in Culture on Cuticle, Journal of Invertebrate Pathology, 48, 85-95 (1986); Todorova, S. I., et al. "Heterogeneity of two *Beauveria bassiana* strains revealed by biochemical tests, protein profiles and bio-assays on *Leptinotarsa decemlineata* (Col.: Chrysomelidae) and *Coleomegilla maculate lengi* (Col.: Coccinellidae) larvae." Entomophaga 39.2 (1994): 159-69; Valadares, M. C. C. and J. L. Azevedo. "Production of amylases and proteases by wild-type and mutant strains of *Metarhizium anisopliae* var. *anisopliae*." Revista de Microbiologia 27.4 (1996): 237-41; Valadares-Inglis, M. C. and J. L. Azevedo. "Amylase and protease secretion in recombinant strains of *Metarhizium anisopliae* var. *anisopliae* following parasexual crosses." Brazilian Journal of Genetics 20.2 (1997): 171-75; Valadares-Inglis, M. C. and J. F. Peberdy. "Location of chitinolytic enzymes in protoplasts and whole cells of the entomopathogenic fungus *Metarhizium anisopliae*." Mycological Research 101.11 (1997): 1393-96; Wang, C. S., M. A. Typas, and T. M. Butt. "Detection and characterisation of pr1 virulent gene deficiencies in the insect pathogenic fungus *Metarhizium anisopliae*." FEMS Microbiology Letters 213.2 (2002): 251-

55; Wei, Z., Y. Q. Cao, and Y. X. Xia. "Cloning of the subtilisin Pr1A gene from a strain of locust specific fungus, *Metarhizium anisopliae*, and functional expression of the protein in *Pichia pastoris*." World Journal of Microbiology and Biotechnology 24.11 (2008): 2481-88; U.S. Pat. No. 5,962,765; WO/2008/063011.

Agriculturally Beneficial Microorganisms:

In at least one embodiment, the biopesticides (i.e., compositions described herein) may optionally comprise one or more additional agriculturally beneficial microorganisms other than those previously described. Alternatively, the one or more additional beneficial microorganisms may be applied either simultaneously or applied sequentially, with the biopesticides disclosed herein. The one or more beneficial microorganisms may be in a spore form, a vegetative form, or a combination thereof. The one or more beneficial microorganisms may include any number of microorganisms having one or more beneficial properties (e.g., produce one or more of the plant signal molecules described herein, enhance nutrient and water uptake, promote and/or enhance nitrogen fixation, enhance growth, enhance seed germination, enhance seedling emergence, break the dormancy or quiescence of a plant, produce or express toxins which supplement and/or enhance the activity of the fungal pesticide (e.g. δ-endotoxin, α-exotoxin, β-exotoxin, etc. produced by *Bacillus thuringiensis*), provide anti-fungal activity, etc.).

In one embodiment, the one or more beneficial microorganisms are diazotrophs (i.e., bacteria which are symbiotic nitrogen-fixing bacteria). In still another embodiment, the one or more diazotrophs are selected from the genera *Rhizobium* spp., *Bradyrhizobium* spp., *Azorhizobium* spp., *Sinorhizobium* spp., *Mesorhizobium* spp., *Azospirillum* spp., and combinations thereof. In still another embodiment, the one or more beneficial microorganisms are bacteria selected from the group consisting of *Rhizobium cellulosilyticum, Rhizobium daejeonense, Rhizobium etli, Rhizobium galegae, Rhizobium gallicum, Rhizobium giardinii, Rhizobium hainanense, Rhizobium huautlense, Rhizobium indigoferae, Rhizobium leguminosarum, Rhizobium loessense, Rhizobium lupini, Rhizobium lusitanum, Rhizobium meliloti, Rhizobium mongolense, Rhizobium miluonense, Rhizobium sullae, Rhizobium tropici, Rhizobium undicola, Rhizobium yanglingense, Bradyrhizobium bete, Bradyrhizobium canariense, Bradyrhizobium elkanii, Bradyrhizobium iriomotense, Bradyrhizobium japonicum, Bradyrhizobium jicamae, Bradyrhizobium liaoningense, Bradyrhizobium pachyrhizi, Bradyrhizobium yuanmingense, Azorhizobium caulinodans, Azorhizobium doebereinerae, Sinorhizobium abri, Sinorhizobium adhaerens, Sinorhizobium americanum, Sinorhizobium aboris Sinorhizobium fredii, Sinorhizobium indiaense, Sinorhizobium kostiense, Sinorhizobium kummerowiae, Sinorhizobium medicae, Sinorhizobium meliloti, Sinorhizobium mexicanus, Sinorhizobium morelense, Sinorhizobium saheli, Sinorhizobium terangae, Sinorhizobium xinjiangense, Mesorhizobium albiziae, Mesorhizobium amorphae, Mesorhizobium chacoense, Mesorhizobium ciceri, Mesorhizobium huakuii, Mesorhizobium loti, Mesorhizobium mediterraneum, Mesorhizobium pluifarium, Mesorhizobium septentrionale, Mesorhizobium ternperatum, Mesorhizobium tianshanense, Azospirillum amazonense, Azospirillum brasilense, Azospirillum canadense, Azospirillum doebereinerae, Azospirillum formosense, Azospirillum halopraeferans, Azospirillum irakense, Azospirillum largimobile, Azospirillum lipoferum, Azospirillum melinis, Azospirillum oryzae, Azospirillum picis, Azospirillum rugosum, Azospirillum thiophilum, Azospirillum zeae*, and combinations thereof.

In a particular embodiment, the one or more diazotrophs are selected from the group consisting of *Bradyrhizobium japonicum, Rhizobium leguminosarum, Rhizobium meliloti, Sinorhizobium meliloti, Azospirillum brasilense*, and combinations thereof. In another embodiment, the beneficial microorganism is *Bradyrhizobium japonicum*. In another embodiment, the beneficial microorganism is *Rhizobium leguminosarum*. In another embodiment, the beneficial microorganism is *Rhizobium meliloti*. In another embodiment, the beneficial microorganism is *Sinorhizobium meliloti*. In another embodiment, the beneficial microorganism is *Azospirillum brasilense*.

In a particular embodiment, the one or more diazotrophs comprises one or more strains of *Rhizobium leguminosarum*. In another particular embodiment, the strain of *R. leguminosarum* comprises the strain SO12A-2-(IDAC 080305-01). In another particular embodiment, the one or more diazotrophs comprises a strain of *Bradyrhizobium japonicum*. In still another particular embodiment, the strain of *Bradyrhizobium japonicum* comprises the strain *B. japonicum* USDA 532C, *B. japonicum* USDA 110, *B. japonicum* USDA 123, *B. japonicum* USDA 127, *B. japonicum* USDA 129, *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50592 (deposited also as NRRL B-59571), *B. japonicum* NRRL B-50593 (deposited also as NRRL B-59572), *B. japonicum* NRRL B-50586 (deposited also as NRRL B-59565), *B. japonicum* NRRL B-50588 (deposited also as NRRL B-59567), *B. japonicum* NRRL B-50587 (deposited also as NRRL B-59566), *B. japonicum* NRRL B-50589 (deposited also as NRRL B-59568), *B. japonicum* NRRL B-50591 (deposited also as NRRL B-59570), *B. japonicum* NRRL B-50590 (deposited also as NRRL B-59569), NRRL B-50594 (deposited also as NRRL B-50493), *B. japonicum* NRRL B-50726, *B. japonicum* NRRL B-50727, *B. japonicum* NRRL B-50728, *B. japonicum* NRRL B-50729, *B. japonicum* NRRL B-50730, and combinations thereof.

In still yet a more particular embodiment, the one or more diazotrophs comprises one or more strains of *R. leguminosarum* comprises the strain SO12A-2-(IDAC 080305-01), *B. japonicum* USDA 532C, *B. japonicum* USDA 110, *B. japonicum* USDA 123, *B. japonicum* USDA 127, *B. japonicum* USDA 129, *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50592 (deposited also as NRRL B-59571), *B. japonicum* NRRL B-50593 (deposited also as NRRL B-59572), *B. japonicum* NRRL B-50586 (deposited also as NRRL B-59565), *B. japonicum* NRRL B-50588 (deposited also as NRRL B-59567), *B. japonicum* NRRL B-50587 (deposited also as NRRL B-59566), *B. japonicum* NRRL B-50589 (deposited also as NRRL B-59568), *B. japonicum* NRRL B-50591 (deposited also as NRRL B-59570), *B. japonicum* NRRL B-50590 (deposited also as NRRL B-59569), NRRL B-50594 (deposited also as NRRL B-50493), *B. japonicum* NRRL B-50726, *B. japonicum* NRRL B-50727, *B. japonicum* NRRL B-50728, *B. japonicum* NRRL B-50729, *B. japonicum* NRRL B-50730, and combinations thereof.

In another embodiment, the one or more beneficial microorganisms comprise one or more phosphate solubilizing microorganisms. Phosphate solubilizing microorganisms include fungal and bacterial strains. In an embodiment, the phosphate solubilizing microorganism are microorganisms selected from the genera consisting of *Acinetobacter* spp., *Arthrobacter* spp., *Arthrobotrys* spp., *Aspergillus* spp., *Azospirillum* spp., *Bacillus* spp., *Burkholderia* spp., *Candida* spp., *Chryseomonas* spp., *Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., and combinations thereof. In still yet another embodiment, the phosphate solubilizing microorganism is a microorganism selected from the group consisting of *Acinetobacter calcoaceticus*, *Arthrobotrys oligospora*, *Aspergillus niger*, *Azospirillum amazonense*, *Azospirillum brasilense*, *Azospirillum canadense*, *Azospirillum doebereinerae*, *Azospirillum formosense*, *Azospirillum halopraeferans*, *Azospirillum irakense*, *Azospirillum largimobile*, *Azospirillum lipoferum*, *Azospirillum melinis*, *Azospirillum oryzae*, *Azospirillum picis*, *Azospirillum rugosum*, *Azospirillum thiophilum*, *Azospirillum zeae*, *Bacillus amyloliquefaciens*, *Bacillus atrophaeus*, *Bacillus circulans*, *Bacillus licheniformis*, *Bacillus subtilis*, *Burkholderia cepacia*, *Burkholderia vietnamiensis*, *Candida krissii*, *Chryseomonas luteola*, *Enterobacter aerogenes*, *Enterobacter asburiae*, *Enterobacter taylorae*, *Eupenicillium parvum*, *Kluyvera cryocrescens*, *Mucor ramosissimus*, *Paecilomyces hepialid*, *Paecilomyces marquandii*, *Paenibacillus macerans*, *Paenibacillus mucilaginosus*, *Penicillium bilaiae* (formerly known as *Penicillium bilaii*), *Penicillium albidum*, *Penicillium aurantiogriseum*, *Penicillium chrysogenum*, *Penicillium citreonigrum*, *Penicillium citrinum*, *Penicillium digitatum*, *Penicillium frequentas*, *Penicillium fuscum*, *Penicillium gaestrivorus*, *Penicillium glabrum*, *Penicillium griseofulvum*, *Penicillium implicatum*, *Penicillium janthinellum*, *Penicillium lilacinum*, *Penicillium minioluteum*, *Penicillium montanense*, *Penicillium nigricans*, *Penicillium oxalicum*, *Penicillium pinetorum*, *Penicillium pinophilum*, *Penicillium purpurogenum*, *Penicillium radicans*, *Penicillium radicum*, *Penicillium raistrickii*, *Penicillium rugulosum*, *Penicillium simplicissimum*, *Penicillium solitum*, *Penicillium variabile*, *Penicillium velutinum*, *Penicillium viridicatum*, *Penicillium glaucum*, *Penicillium fussiporus*, and *Penicillium expansum*, *Pseudomonas corrugate*, *Pseudomonas fluorescens*, *Pseudomonas lutea*, *Pseudomonas poae*, *Pseudomonas putida*, *Pseudomonas stutzeri*, *Pseudomonas trivialis*, *Serratia marcescens*, *Stenotrophomonas maltophilia*, *Swaminathania salitolerans*, *Thiobacillus ferrooxidans*, *Torulospora globosa*, *Vibrio proteolyticus*, *Xanthobacter agilis*, *Xanthomonas campestris*, and combinations thereof.

In a particular embodiment, the one or more phosphate solubilizing microorganisms is a strain of the fungus *Penicillium*. In another embodiment, the one or more *Penicillium* species is *P. bilaiae*, *P. gaestrivorus*, or combinations thereof. In a particular embodiment, the strain of *Penicillium* comprises *P. bilaiae* NRRL 50169, *P. bilaiae* ATCC 20851, *P. bilaiae* ATCC 22348, *P. bilaiae* ATCC 18309, *P. bilaiae* NRRL 50162 and combinations thereof. In another particular embodiment, the strain of *Penicillium* comprises strain *P. gaestrivorus* NRRL 50170. In still yet another particular embodiment, the strain of *Penicillium* comprises *P. bilaiae* NRRL 50169, *P. bilaiae* ATCC 20851, *P. bilaiae* ATCC 22348, *P. bilaiae* ATCC 18309, *P. bilaiae* NRRL 50162, *P. gaestrivorus* NRRL 50170, and combinations thereof.

In another embodiment the beneficial microorganism is one or more mycorrhiza. In particular, the one or more mycorrhiza is an endomycorrhiza (also called vesicular arbuscular mycorrhizas, VAMs, arbuscular mycorrhizas, or AMs), an ectomycorrhiza, or a combination thereof.

In one embodiment, the one or more mycorrhiza is an endomycorrhiza of the phylum Glomeromycota and genera *Glomus* and *Gigaspora*. In still a further embodiment, the endomycorrhiza is a strain of *Glomus aggregatum*, *Glomus brasilianum*, *Glomus clarum*, *Glomus deserticola*, *Glomus etunicatum*, *Glomus fasciculatum*, *Glomus intraradices*, *Glomus monosporum*, or *Glomus mosseae*, *Gigaspora margarita*, or a combination thereof.

In another embodiment, the one or more mycorrhiza is an ectomycorrhiza of the phylum Basidiomycota, Ascomycota, and Zygomycota. In still yet another embodiment, the ectomycorrhiza is a strain of *Laccaria bicolor*, *Laccaria laccata*, *Pisolithus tinctorius*, *Rhizopogon amylopogon*, *Rhizopogon fulvigleba*, *Rhizopogon luteolus*, *Rhizopogon villosuli*, *Scleroderma cepa*, *Scleroderma citrinum*, or a combination thereof.

In still another embodiment, the one or more mycorrhiza is an ericoid mycorrhiza, an arbutoid mycorrhiza, or a monotropoid mycorrhiza. Arbuscular and ectomycorrhizas form ericoid mycorrhiza with many plants belonging to the order Ericales, while some Ericales form arbutoid and monotropoid mycorrhizas. All orchids are mycoheterotrophic at some stage during their lifecycle and form orchid mycorrhizas with a range of basidiomycete fungi. In one embodiment, the mycorrhiza may be an ericoid mycorrhiza, preferably of the phylum Ascomycota, such as *Hymenoscyphous ericae* or *Oidiodendron* sp. In another embodiment, the mycorrhiza also may be an arbutoid mycorrhiza, preferably of the phylum Basidiomycota. In yet another embodiment, the mycorrhiza may be a monotripoid mycorrhiza, preferably of the phylum Basidiomycota. In still yet another embodiment, the mycorrhiza may be an orchid mycorrhiza, preferably of the genus *Rhizoctonia*.

In still another embodiment, the one or more beneficial microorganisms are microorganisms capable of exhibiting fungicidal activity, (e.g., biofungicides). Non-limiting examples of biofungicides include, *Ampelomyces quisqualis* (e.g., AQ 10® from Intrachem Bio GmbH & Co. KG, Germany), *Aspergillus flavus* (e.g., AFLAGUARD® from Syngenta, CH), *Aureobasidium pullulans* (e.g., BOTECTOR® from bio-ferm GmbH, Germany), *Bacillus amyloliquefaciens* FZB24 (e.g., isolates NRRL B-50304 and NRRL B-50349 TAEGRO® from Novozymes Biologicals, Inc., USA), *Bacillus subtilis* (e.g., isolate NRRL B-21661 in RHAPSODY®, SERENADE® MAX and SERENADE® ASO from Bayer CropScience, Gustafson), *Bacillus pumilus* (e.g., isolate NRRL B-50349 from Bayer CropScience, Gustafson), *Bacillus amyloliquefaciens* TrigoCor (also known as "TrigoCor 1448"; e.g., isolate Embrapa Trigo Accession No. 144/88.4Lev, Cornell Accession No. Pma007BR-97, and ATCC Accession No. 202152, from Cornell University, USA), *Candida oleophila* 1-82 (e.g., ASPIRE® from Ecogen Inc., USA), *Candida saitoana* (e.g., BIOCURE® (in mixture with lysozyme) and BIOCOAT® from Micro Flo Company, USA (BASF SE) and Arysta), Chitosan (e.g., ARMOUR-ZEN from BotriZen Ltd., NZ), *Chromobacterium subtsugae* (e.g., isolate NRRL B-30655 from United States Department of Agriculture, USA), *Clonostachys rosea* f. *catenulata*, also named *Gliocladium catenulatum* (e.g., isolate J1446: PRESTOP® from Verdera, Finland), *Coniothyrium minitans* (e.g., CONTANS® from Prophyta, Germany), *Cryphonectria parasitica* (e.g., *Endothia parasitica* from CNICM, France), *Cryptococcus albidus* (e.g., YIELD PLUS® from Anchor Bio-Technologies, South Africa), *Fusarium oxysporum* (e.g., BIOFOX® from S.I.A.P.A., Italy, FUSACLEAN® from Natural Plant Protection, France), *Metschnikowia fructicola* (e.g., SHEMER® from Agrogreen, Israel), *Microdochium dimerum* (e.g., ANTIBOT® from Agrauxine, France), *Paecilomyces fumosoroseus* FE991 (in NOFLY® from FuturEco BioScience S.L., Barcelona, Spain), *Phlebiopsis gigantea* (e.g., ROTSOP® from Verdera, Finland), *Pseudozyma flocculosa* (e.g., SPORODEX® from Plant Products Co. Ltd., Canada), *Pythium oligandrum* DV74 (e.g., POLYVERSUM® from Remeslo SSRO, Biopreparaty, Czech Rep.), *Reynoutria sachlinensis* (e.g., REGALIA® from Marrone BioInnovations, USA), *Talaromyces flavus* V117b (e.g., PROTUS® from Prophyta, Germany), *Trichoderma asperellum* SKT-1 (e.g., ECO-HOPE® from Kumiai Chemical Industry Co., Ltd., Japan), *T. atroviride* LC52 (e.g., SENTINEL® from Agrimm Technologies Ltd, NZ), *T. harzianum* T-22 (e.g., PLANTSHIELD® der Firma BioWorks Inc., USA), *T. harzianum* TH 35 (e.g., ROOT PRO® from Mycontrol Ltd., Israel), *T. harzianum* T-39 (e.g., TRICHODEX® and *TRICHODERMA* 2000® from Mycontrol Ltd., Israel and Makhteshim Ltd., Israel), *T. harzianum* and *T. viride* (e.g., TRICHOPEL from Agrimm Technologies Ltd, NZ), *T. harzianum* ICC012 and *T. viride* ICC080 (e.g., REMEDIER® WP from Isagro Ricerca, Italy), *T. polysporum* and *T. harzianum* (e.g., BINAB® from BINAB Bio-Innovation AB, Sweden), *T. stromaticum* (e.g., TRICOVAB® from C.E.P.L.A.C., Brazil), *T. virens* GL-21 (e.g., SOILGARD® from Certis LLC, USA), *T. viride* (e.g., TRIECO® from Ecosense Labs. (India) Pvt. Ltd., Indien, BIO-CURE® F from T. Stanes & Co. Ltd., Indien), *T. viride* TV1 (e.g., *T. viride* TV1 from Agribiotec srl, Italy), *Streptomyces lydicus* WYEC 108 (e.g., isolate ATCC 55445 in ACTINOVATE®, ACTINOVATE AG®, ACTINOVATE STP®, ACTINO-IRON®, ACTINOVATE L&G®, and ACTINOGROW® from Idaho Research Foundation, USA), *Streptomyces violaceusniger* WYEC 108 (e.g., isolate ATCC 55660 in DE-THATCH-9®, DECOMP-9®, and THATCH CONTROL® from Idaho Research Foundation, USA), *Streptomyces* WYE 53 (e.g., isolate ATCC 55750 in DE-THATCH-9®, DECOMP-9®, and THATCH CONTROL® from Idaho Research Foundation, USA), and *Ulocladium oudemansii* HRU3 (e.g., BOTRY-ZEN® from Botry-Zen Ltd, NZ).

Plant Signal Molecule(s):

In at least one embodiment, the biopesticides (i.e., compositions described herein) may optionally comprise one or more plant signal molecules. Alternatively, the one or more plant signal molecules may be applied either simultaneously or applied sequentially, with the biopesticides disclosed herein. In an embodiment, the biopesticides (i.e., compositions described herein) may include one or more plant signal molecules. In one embodiment, the one or more plant signal molecules are one or more LCOs. In another embodiment, the one or more plant signal molecules are one or more COs. In still another embodiment, the one or more plant signal molecules are one or more chitinous compounds. In yet another embodiment, the one or more plant signal molecules are one or more non-flavonoid nod gene inducers (e.g., jasmonic acid, linoleic acid, linolenic acid, and derivatives thereof). In still yet another embodiment, the one or more plant signal molecules are one or more karrikins or derivatives thereof. In still another embodiment, the one or more plant signal molecules are one or more LCOs, one or more COs, one or more chitinous compounds, one or more non-flavonoid nod gene inducers and derivatives thereof, one or more karrikins and derivatives thereof, or any signal molecule combination thereof.

LCOs:

Lipo-chitooligosaccharide compounds (LCOs), also known in the art as symbiotic Nod signals or Nod factors, consist of an oligosaccharide backbone of β-1,4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and non-reducing sugar residues. LCOs are intended to include all LCOs as well as isomers, salts, and solvates thereof. An example of an LCO is presented below as formula I:

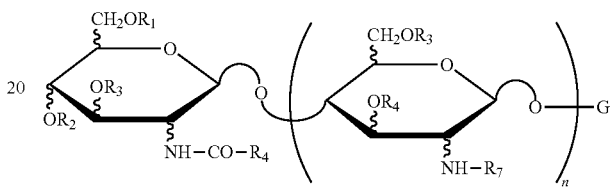

in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3$ CO—, $C_xH_y$ CO— where x is an integer between 0 and 17, and y is an integer between 1 and 35, or any other acyl group such as for example a carbamyl, $R_4$ represents a mono-, di-, tri- and tetraunsaturated aliphatic chain containing at least 12 carbon atoms, and n is an integer between 1 and 4.

LCOs may be obtained (isolated and/or purified) from bacteria such as *Rhizobia*, e.g., *Rhizobium* spp., *Bradyrhizobium* spp., *Sinorhizobium* spp. and *Azorhizobium* spp. LCO structure is characteristic for each such bacterial species, and each strain may produce multiple LCO's with different structures. For example, specific LCOs from *S. meliloti* have also been described in U.S. Pat. No. 5,549,718 as having the formula II:

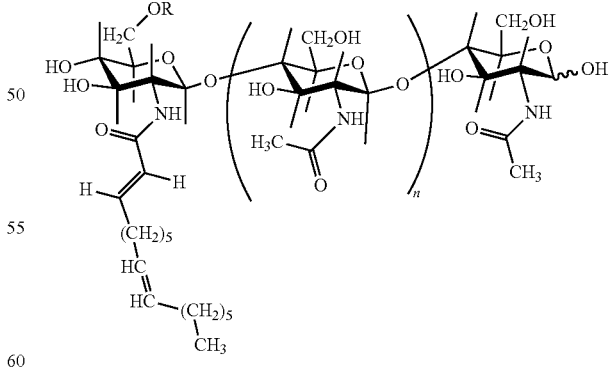

in which R represents H or $CH_3CO$— and n is equal to 2 or 3.

Even more specific LCOs include NodRM, NodRM-1, NodRM-3. When acetylated (the R=$CH_3$ CO—), they become AcNodRM-1, and AcNodRM-3, respectively (U.S. Pat. No. 5,545,718).

LCOs from *Bradyrhizobium japonicum* are described in U.S. Pat. Nos. 5,175,149 and 5,321,011. Broadly, they are pentasaccharide phytohormones comprising methylfucose. A number of these *B. japonicum*-derived LCOs are described: BjNod-V ($C_{18:1}$); BjNod-V ($A_C$, $C_{18:1}$), BjNod-V ($C_{16:1}$); and BjNod-V ($A_C$, $C_{16:0}$), with "V" indicating the presence of five N-acetylglucosamines; "Ac" an acetylation; the number following the "C" indicating the number of carbons in the fatty acid side chain; and the number following the ":" the number of double bonds.

LCOs used in compositions of the invention may be obtained (i.e., isolated and/or purified) from bacterial strains that produce LCO's, such as strains of *Azorhizobium*, *Bradyrhizobium* (including *B. japonicum*), *Mesorhizobium*, *Rhizobium* (including *R. leguminosarum*), *Sinorhizobium* (including *S. meliloti*), and bacterial strains genetically engineered to produce LCO's.

Also encompassed by the present invention are compositions using LCOs obtained (i.e., isolated and/or purified) from a mycorrhizal fungus, such as fungi of the group Glomerocycota, e.g., *Glomus intraradicus*. The structures of representative LCOs obtained from these fungi are described in WO 2010/049751 and WO 2010/049751 (the LCOs described therein also referred to as "Myc factors").

Further encompassed by compositions of the present invention is use of synthetic LCO compounds, such as those described in WO 2005/063784, and recombinant LCO's produced through genetic engineering. The basic, naturally occurring LCO structure may contain modifications or substitutions found in naturally occurring LCO's, such as those described in Spaink, Crit. Rev. Plant Sci. 54:257-288 (2000) and D'Haeze, et al., Glycobiology 12:79R-105R (2002). Precursor oligosaccharide molecules (COs, which as described below, are also useful as plant signal molecules in the present invention) for the construction of LCOs may also be synthesized by genetically engineered organisms, e.g., as in Samain, et al., Carb. Res. 302:35-42 (1997); Samain, et al., J. Biotechnol. 72:33-47 (1999).

LCO's may be utilized in various forms of purity and may be used alone or in the form of a culture of LCO-producing bacteria or fungi. Methods to provide substantially pure LCO's include simply removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage.

COs:

Chitooligosaccharides (COs) are known in the art as β-1-4 linked N actyl glucosamine structures identified as chitin oligomers, also as N-acetylchitooligosaccharides. CO's have unique and different side chain decorations which make them different from chitin molecules [$(C_8H_{13}NO_5)n$, CAS No. 1398-61-4], and chitosan molecules [$(C_5H_{11}NO_4)n$, CAS No. 9012-76-4]. Representative literature describing the structure and production of COs is as follows: Van der Holst, et al., Current Opinion in Structural Biology, 11:608-616 (2001); Robina, et al., Tetrahedron 58:521-530 (2002); Hanel, et al., Planta 232:787-806 (2010); Rouge, et al. Chapter 27, "The Molecular Immunology of Complex Carbohydrates" in Advances in Experimental Medicine and Biology, Springer Science; Wan, et al., Plant Cell 21:1053-69 (2009); PCT/F100/00803 (Sep. 21, 2000); and Demont-Caulet, et al., Plant Physiol. 120(1):83-92 (1999). The COs may be synthetic or recombinant. Methods for preparation of recombinant COs are known in the art. See, e.g., Samain, et al. (supra.); Cottaz, et al., Meth. Eng. 7(4):311-7 (2005) and Samain, et al., J. Biotechnol. 72:33-47 (1999). COs are intended to include isomers, salts, and solvates thereof.

Chitinous Compounds:

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4,5-dihydroxy-6-(hydroxymethyl)oxan-2yl] methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), chitosan, (IUPAC: 5-amino-6-[5-amino-6-[5-amino-4,6-dihydroxy-2(hydroxymethyl)oxan-3-yl]oxy-4-hydroxy-2-(hydroxymethyl) oxan-3-yl]oxy-2(hydroxymethyl)oxane-3,4-diol), and isomers, salts, and solvates thereof.

These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965,545 (preparation from crab shells and hydrolysis of commercial chitosan). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are also commercially available. Commercial products include, for example, ELEXA® (Plant Defense Boosters, Inc.) and BEYOND™ (Agrihouse, Inc.).

Flavonoids:

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include are known in the art. See, Jain, et al., J. Plant Biochem. & Biotechnol. 11:1-10 (2002); Shaw, et al., Environmental Microbiol. 11:1867-80 (2006). Flavonoid compounds are commercially available, e.g., from Novozymes BioAg, Saskatoon, Canada; Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston, et al., Plant Physiology 137:1375-88 (2005). Flavonoid compounds are intended to include all flavonoid compounds as well as isomers, salts, and solvates thereof.

The one or more flavonoids may be a natural flavonoid (i.e., not synthetically produced), a synthetic flavonoid (e.g., a chemically synthesized flavonoid) or a combination thereof. In a particular embodiment, the compositions described herein comprise a flavanol, a flavone, an anthocyanidin, an isoflavonoid, a neoflavonoid and combinations thereof, including all isomer, solvate, hydrate, polymorphic, crystalline form, non-crystalline form, and salt variations thereof.

In an embodiment, the compositions described herein may comprise one or more flavanols. In still another embodiment, the compositions described herein may comprise one or more flavanols selected from the group consisting of flavan-3-ols (e.g., catechin (C), gallocatechin (GC), catechin 3-gallate (Cg), gallcatechin 3-gallate (GCg), epicatechins (EC), epigallocatechin (EGC) epicatechin 3-gallate (ECg), epigallcatechin 3-gallate (EGCg), etc.), flavan-4-ols, flavan-3,4-diols (e.g., leucoanthocyanidin), proanthocyanidins (e.g., includes dimers, trimer, oligomers, or polymers of flavanols), and combinations thereof. In still yet another embodiment, the compositions described herein may comprise one or more flavanols selected from the group consisting of catechin (C), gallocatechin (GC), catechin 3-gallate (Cg), gallcatechin 3-gallate (GCg), epicatechins (EC), epigallocatechin (EGC) epicatechin 3-gallate (ECg), epigallcatechin 3-gallate (EGCg), flavan-4-ol, leucoanthocyanidin, and dimers, trimers, olilgomers or polymers thereof.

In another embodiment, the compositions described herein may comprise one or more flavones. In still another embodiment, the compositions described herein may comprise one or more flavones selected from the group consisting of flavones (e.g., luteolin, apigenin, tangeritin, etc.), flavonols (e.g., quercetin, quercitrin, rutin, kaempferol, kaempferitrin, astragalin, sophoraflavonoloside, myricetin, fisetin, isorhamnetin, pachypodol, rhamnazin, etc.), flavanones (e.g. hesperetin, hesperidin, naringenin, eriodictyol, homoeriodictyol, etc.), and flavanonols (e.g., dihydroquercetin, dihydrokaempferol, etc.). In still yet another embodiment, the compositions described herein may comprise one or more flavones selected from the group consisting of luteolin, apigenin, tangeritin, quercetin, quercitrin, rutin, kaempferol, kaempferitrin, astragalin, sophoraflavonoloside, myricetin, fisetin, isorhamnetin, pachypodol, rhamnazin, hesperetin, hesperidin, naringenin, eriodictyol, homoeriodictyol, dihydroquercetin, dihydrokaempferol, and combinations thereof.

In still another embodiment, the compositions described herein may comprise one or more anthocyanidins. In yet another embodiment, the compositions described herein may comprise one or more anthocyanidins selected from the group selected from the group consisting of cyanidins, delphinidins, malvidins, pelargonidins, peonidins, petunidins, and combinations thereof.

In another embodiment, the compositions described herein may comprise one or more isoflavonoids. In still yet another embodiment, the compositions described herein comprise one or more isoflavonoids selected from the group consisting of phytoestrogens, isoflavones (e.g., genistein, daidzein, glycitein, etc.), and isoflavanes (e.g., equol, lonchocarpane, laxiflorane, etc.), and combinations thereof. In yet another embodiment the compositions described herein may comprise one or more isoflavonoids selected from the group consisting of genistein, daidzein, glycitein, equol, lonchocarpane, laxiflorane, and combinations thereof.

In another embodiment, the compositions described herein may comprise one or more neoflavonoids. In yet another embodiment, the compositions described herein may comprise one or more neoflavonoids selected from the group consisting of neoflavones (e.g., calophyllolide), neoflavenes (e.g., dalbergichromene), coutareagenins, dalbergins, nivetins, and combinations thereof. In still yet another embodiment, the compositions described herein may comprise one or more neoflavonoids selected from the group consisting of calophyllolide, dalbergichromene, coutareagenin, dalbergin, nivetin, and combinations thereof.

In another embodiment, the compositions described herein may comprise one or flavonoids selected from the group consisting of catechin (C), gallocatechin (GC), catechin 3-gallate (Cg), gallcatechin 3-gallate (GCg), epicatechins (EC), epigallocatechin (EGC) epicatechin 3-gallate (ECg), epigallcatechin 3-gallate (EGCg), flavan-4-ol, leucoanthocyanidin, proanthocyanidins, luteolin, apigenin, tangeritin, quercetin, quercitrin, rutin, kaempferol, kaempferitrin, astragalin, sophoraflavonoloside, myricetin, fisetin, isorhamnetin, pachypodol, rhamnazin, hesperetin, hesperidin, naringenin, eriodictyol, homoeriodictyol, dihydroquercetin, dihydrokaempferol, cyanidins, delphinidins, malvidins, pelargonidins, peonidins, petunidins, genistein, daidzein, glycitein, equol, lonchocarpane, laxiflorane, calophyllolide, dalbergichromene, coutareagenin, dalbergin, nivetin, and combinations thereof. In still another embodiment, the compositions described herein may comprise one or more flavonoids selected from the group consisting of hesperetin, hesperidin, naringenin, genistein, daidzein, and combinations thereof. In a particular embodiment, the composition described herein may comprise the flavonoid hesperetin. In another particular embodiment, the composition described herein may comprise the flavonoid hesperidin. In still another particular embodiment, the composition described herein may comprise the flavonoid naringenin. In still yet another particular embodiment, the composition described herein may comprise the flavonoid genistein. In yet still another particular embodiment, the composition described herein may comprise the flavonoid daidzein.

Non-Flavonoid Nod-Gene Inducer(s):

Jasmonic acid (JA, [1R-[1α,2β(Z)]]-3-oxo-2-(pentenyl) cyclopentaneacetic acid) and its derivatives, linoleic acid ((Z,Z)-9,12-Octadecadienoic acid) and its derivatives, and linolenic acid ((Z,Z,Z)-9,12,15-octadecatrienoic acid) and its derivatives, may also be used in the compositions described herein. Non-flavonoid nod-gene inducers are intended to include not only the non-flavonoid nod-gene inducers described herein, but isomers, salts, and solvates thereof.

Jasmonic acid and its methyl ester, methyl jasmonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibberella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Jasmonates, linoleic acid and linolenic acid (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001; and Mabood, Fazli, "Linoleic and linolenic acid induce the expression of nod genes in *Bradyrhizobium japonicum*," USDA 3, May 17, 2001.

Useful derivatives of linoleic acid, linolenic acid, and jasmonic acid that may be useful in compositions of the present invention include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an $NR^2R^3$ group, in which $R^2$ and $R^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid, and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Karrikin(s):

Karrikins are vinylogous 4H-pyrones e.g., 2H-furo[2,3-c]pyran-2-ones including derivatives and analogues thereof. It is intended that the karrikins include isomers, salts, and solvates thereof. Examples of these compounds are represented by the following structure:

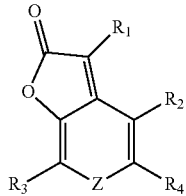

wherein; Z is O, S or $NR_5$; $R_1$, $R_2$, $R_3$, and $R_4$ are each independently H, alkyl, alkenyl, alkynyl, phenyl, benzyl, hydroxy, hydroxyalkyl, alkoxy, phenyloxy, benzyloxy, CN, $COR_6$, COOR=, halogen, $NR_6R_7$, or $NO_2$; and $R_5$, $R_6$, and $R_7$ are each independently H, alkyl or alkenyl, or a biologically acceptable salt thereof. Examples of biologically acceptable salts of these compounds may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by the structure and which may be suitable for use in the present invention include the following: 3-methyl-2H-furo[2,3-c]pyran-2-one (where $R_1$=$CH_3$, $R_2$, $R_3$, $R_4$=H), 2H-furo[2,3-c]pyran-2-one (where $R_1$, $R_2$, $R_3$, R4=H), 7-methyl-2H-furo[2,3-c]pyran-2-one (where $R_1$, $R_2$, $R_4$=H, $R_3$=$CH_3$), 5-methyl-2H-furo[2,3-c]pyran-2-one (where $R_1$, $R_2$, $R_3$=H, $R_4$=$CH_3$), 3,7-dimethyl-2H-furo[2,3-c]pyran-2-one (where $R_1$, $R_3$=$CH_3$, $R_2$, $R_4$=H), 3,5-dimethyl-2H-furo[2,3-c]pyran-2-one (where $R_1$, $R_4$=$CH_3$, $R_2$, $R_3$=H), 3,5,7-trimethyl-2H-furo[2,3-c]pyran-2-one (where $R_1$, $R_3$, $R_4$=$CH_3$, $R_{2=H}$), 5-methoxymethyl-3-methyl-2H-furo[2,3-c]pyran-2-one (where $R_1$=$CH_3$, $R_2$, $R_3$=H, $R_4$=$CH_2OCH_3$), 4-bromo-3,7-dimethyl-2H-furo[2,3-c]pyran-2-one (where $R_1$, $R_3$=$CH_3$, $R_2$=Br, $R_4$=H), 3-methylfuro[2,3-c]pyridin-2(3H)-one (where Z=NH, $R_1$=$CH_3$, $R_2$, $R_3$, $R_4$=H), 3,6-dimethylfuro[2,3-c]pyridin-2(6H)-one (where Z=N—$CH_3$, $R_1$=$CH_3$, $R_2$, $R_3$, $R_4$=H). See, U.S. Pat. No. 7,576,213. These molecules are also known as karrikins. See, Halford, "Smoke Signals," in Chem. Eng. News (Apr. 12, 2010), at pages 37-38 (reporting that karrikins or butenolides which are contained in smoke act as growth stimulants and spur seed germination after a forest fire, and can invigorate seeds such as corn, tomatoes, lettuce and onions that had been stored). These molecules are the subject of U.S. Pat. No. 7,576,213.

Metabolites:

In at least one embodiment, the biopesticides (i.e., compositions described herein) may optionally comprise one or more metabolites. Alternatively, the one or more metabolites may be applied either simultaneously or applied sequentially, with the biopesticides disclosed herein. In one embodiment, the one or more metabolites may be used to enhance the activity of the fungal pesticides herein. Non-limiting examples of metabolites that may be used in the compositions disclosed herein are described in Anke, H. "Insecticidal and Nematicidal Metabolites from Fungi. Industrial Applications, 2nd ed. The Mycota X" (M. Hofrichter, ed.), (2010): Springer-Verlag Berlin Heidelberg, 151-163. In one embodiment, non-limiting examples of metabolites include alkaloids, peptides, cyclic peptides, cyclic depsipeptides, quinolone derivatives, nodulisporic acids, paraherquamide metabolites, nafuredin, and combinations thereof.

Nutrient(s):

In at least one embodiment, the biopesticides (i.e., compositions described herein) may optionally comprise one or more nutrients. Alternatively, the one or more nutrients may be applied either simultaneously or applied sequentially, with the biopesticides disclosed herein. Non-limiting examples of nutrients for use in the biopesticides described herein include vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutein, lycopene, zeaxanthin, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), organic acids (e.g., acetic acid, citric acid, lactic acid, malic acid, taurine, etc.), and combinations thereof. In a particular embodiment, the biopesticides may comprise phosphorous, boron, chlorine, copper, iron, manganese, molybdenum, zinc or combinations thereof.

In certain embodiments, where the biopesticides described herein may comprise phosphorous, it is envisioned that any suitable source of phosphorous may be provided. In one embodiment, the phosphorus may be derived from a source. In another embodiment, suitable sources of phosphorous include phosphorous sources capable of solubilization by one or more microorganisms (e.g., *Penicillium bilaiae*, as well as other phosphate solubilizing strains described herein, etc.).

In one embodiment, the phosphorus may be derived from a rock phosphate source. In another embodiment the phosphorous may be derived from fertilizers comprising one or more phosphorous sources. Commercially available manufactured phosphate fertilizers are of many types. Some common ones are those containing rock phosphate, monoammonium phosphate, diammonium phosphate, monocalcium phosphate, super phosphate, triple super phosphate, and/or ammonium polyphosphate. All of these fertilizers are produced by chemical processing of insoluble natural rock phosphates in large scale fertilizer-manufacturing facilities and the product is expensive. By means of the present invention it is possible to reduce the amount of these fertilizers applied to the soil while still maintaining the same amount of phosphorus uptake from the soil.

In still another embodiment, the phosphorous may be derived from an organic phosphorous source. In a further particular embodiment, the source of phosphorus may include an organic fertilizer. An organic fertilizer refers to a soil amendment derived from natural sources that guarantees, at least, the minimum percentages of nitrogen, phosphate, and potash. Non-limiting examples of organic fertilizers include plant and animal by-products, rock powders, seaweed, inoculants, and conditioners. These are often available at garden centers and through horticultural supply companies. In particular the organic source of phosphorus is from bone meal, meat meal, animal manure, compost, sewage sludge, or guano, or combinations thereof.

In still another embodiment, the phosphorous may be derived from a combination of phosphorous sources including, but not limited to, rock phosphate, fertilizers comprising one or more phosphorous sources (e.g., monoammonium phosphate, diammonium phosphate, monocalcium phosphate, super phosphate, triple super phosphate, ammonium polyphosphate, etc.) one or more organic phosphorous sources, and combinations thereof.

Biostimulant(s):

In at least one embodiment, the biopesticides (i.e., compositions described herein) may optionally comprise one or more biostimulants. Alternatively, the one or more biostimulants may be applied either simultaneously or applied sequentially, with the biopesticides disclosed herein. Biostimulants may enhance metabolic or physiological processes such as respiration, photosynthesis, nucleic acid uptake, ion uptake, nutrient delivery, or a combination thereof. Non-limiting examples of biostimulants include seaweed extracts (e.g., ascophyllum nodosum), humic acids (e.g., potassium humate), fulvic acids, myo-inositol, glycine, and combinations thereof. In another embodiment, the compositions comprise seaweed extracts, humic acids, fulvic acids, myo-inositol, glycine, and combinations thereof.

Herbicide(s):

In at least one embodiment, the biopesticides (i.e., compositions described herein) may optionally comprise one or more herbicides. Alternatively, the one or more herbicides may be applied either simultaneously or applied sequentially, with the biopesticides disclosed herein. In a particular embodiment, the herbicide may be a pre-emergent herbicide, a post-emergent herbicide, or a combination thereof.

Suitable herbicides include chemical herbicides, natural herbicides (e.g., bioherbicides, organic herbicides, etc.), or combinations thereof. Non-limiting examples of suitable herbicides include bentazon, acifluorfen, chlorimuron, lactofen, clomazone, fluazifop, glufosinate, glyphosate, sethoxydim, imazethapyr, imazamox, fomesafe, flumiclorac, imazaquin, and clethodim. Commercial products containing each of these compounds are readily available. Herbicide concentration in the composition will generally correspond to the labeled use rate for a particular herbicide.

Fungicide(s):

In at least one embodiment, the biopesticides (i.e., compositions described herein) may optionally comprise one or more fungicides. Alternatively, the one or more fungicides may be applied either simultaneously or applied sequentially, with the biopesticides disclosed herein. Fungicides useful to the compositions described herein may be biological fungicides, chemical fungicides, or combinations thereof. Fungicides may be selected so as to be provide effective control against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). More common fungal pathogens that may be effectively targeted include *Pytophthora, Rhizoctonia, Fusarium, Pythium, Phomopsis* or *Selerotinia* and *Phakopsora* and combinations thereof.

Non-limiting examples of biological fungicides that may be suitable for use with the biopesticides disclosed herein include *Ampelomyces quisqualis* (e.g., AQ 10® from Intrachem Bio GmbH & Co. KG, Germany), *Aspergillus flavus* (e.g., AFLAGUARD® from Syngenta, CH), *Aureobasidium pullulans* (e.g., BOTECTOR® from bio-ferm GmbH, Germany), *Bacillus amyloliquefaciens* FZB24 (e.g., isolates NRRL B-50304 and NRRL B-50349 TAEGRO® from Novozymes Biologicals, Inc., USA), *Bacillus subtilis* (e.g., isolate NRRL B-21661 in RHAPSODY®, SERENADE® MAX and SERENADE® ASO from Bayer CropScience, Gustafson), *Bacillus pumilus* (e.g., isolate NRRL B-50349 from Bayer CropScience, Gustafson), *Bacillus amyloliquefaciens* TrigoCor (also known as "TrigoCor 1448"; e.g., isolate Embrapa Trigo Accession No. 144/88.4Lev, Cornell Accession No. Pma007BR-97, and ATCC Accession No. 202152, from Cornell University, USA), *Candida oleophila* 1-82 (e.g., ASPIRE® from Ecogen Inc., USA), *Candida saitoana* (e.g., BIOCURE® (in mixture with lysozyme) and BIOCOAT® from Micro Flo Company, USA (BASF SE) and Arysta), Chitosan (e.g., ARMOUR-ZEN from BotriZen Ltd., NZ), *Chromobacterium subtsugae* (e.g., isolate NRRL B-30655 from United States Department of Agriculture, USA), *Clonostachys rosea* f. *catenulata*, also named *Gliocladium catenulatum* (e.g., isolate J1446: PRESTOP® from Verdera, Finland), *Coniothyrium minitans* (e.g., CONTANS® from Prophyta, Germany), *Cryphonectria parasitica* (e.g., *Endothia parasitica* from CNICM, France), *Cryptococcus albidus* (e.g., YIELD PLUS® from Anchor Bio-Technologies, South Africa), *Fusarium oxysporum* (e.g., BIOFOX® from S.I.A.P.A., Italy, FUSACLEAN® from Natural Plant Protection, France), *Metschnikowia fructicola* (e.g., SHEMER® from Agrogreen, Israel), *Microdochium dimerum* (e.g., ANTIBOT® from Agrauxine, France), *Paecilomyces fumosoroseus* FE991 (in NOFLY® from FuturEco BioScience S.L., Barcelona, Spain), *Phlebiopsis gigantea* (e.g., ROTSOP® from Verdera, Finland), *Pseudozyma flocculosa* (e.g., SPORODEX® from Plant Products Co. Ltd., Canada), *Pythium oligandrum* DV74 (e.g., POLYVERSUM® from Remeslo SSRO, Biopreparaty, Czech Rep.), *Reynoutria sachlinensis* (e.g., REGA- LIA® from Marrone BioInnovations, USA), *Talaromyces flavus* V117b (e.g., PROTUS® from Prophyta, Germany), *Trichoderma asperellum* SKT-1 (e.g., ECO-HOPE® from Kumiai Chemical Industry Co., Ltd., Japan), *T. atroviride* LC52 (e.g., SENTINEL® from Agrimm Technologies Ltd, NZ), *T. harzianum* T-22 (e.g., PLANTSHIELD® der Firma BioWorks Inc., USA), *T. harzianum* TH 35 (e.g., ROOT PRO® from Mycontrol Ltd., Israel), *T. harzianum* T-39 (e.g., TRICHODEX® and *TRICHODERMA* 2000® from Mycontrol Ltd., Israel and Makhteshim Ltd., Israel), *T. harzianum* and *T. viride* (e.g., TRICHOPEL from Agrimm Technologies Ltd, NZ), *T. harzianum* ICC012 and *T. viride* ICC080 (e.g., REMEDIER® WP from Isagro Ricerca, Italy), *T. polysporum* and *T. harzianum* (e.g., BINAB® from BINAB Bio-Innovation AB, Sweden), *T. stromaticum* (e.g., TRICOVAB® from C.E.P.L.A.C., Brazil), *T. virens* GL-21 (e.g., SOILGARD® from Certis LLC, USA), *T. viride* (e.g., TRIECO® from Ecosense Labs. (India) Pvt. Ltd., Indien, BIO-CURE® F from T. Stanes & Co. Ltd., Indien), *T. viride* TV1 (e.g., *T. viride* TV1 from Agribiotec srl, Italy), *Streptomyces lydicus* WYEC 108 (e.g., isolate ATCC 55445 in ACTINOVATE®, ACTINOVATE AG®, ACTINOVATE STP®, ACTINO-IRON®, ACTINOVATE L&G®, and ACTINOGROW® from Idaho Research Foundation, USA), *Streptomyces violaceusniger* WYEC 108 (e.g., isolate ATCC 55660 in DE-THATCH-9®, DECOMP-9®, and THATCH CONTROL® from Idaho Research Foundation, USA), *Streptomyces* WYE 53 (e.g., isolate ATCC 55750 in DE-THATCH-9®, DECOMP-9®, and THATCH CONTROL® from Idaho Research Foundation, USA), and *Ulocladium oudemansii* HRU3 (e.g., BOTRY-ZEN® from Botry-Zen Ltd, NZ).

Representative examples of chemical fungicides that may be suitable for use in the present invention include A) strobilurins:

azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide;

B) carboxamides:

carboxanilides: benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyra-zole-4-carboxamide and N-(2-(1,3,3-trimethylbutyl)-phenyl)-1,3-dimethyl-5-fluoro-1H-pyrazole-4-carboxamide;

carboxylic morpholides: dimethomorph, flumorph, pyrimorph;

benzoic acid amides: flumetover, fluopicolide, fluopyram, zoxamide;

other carboxamides: carpropamid, dicyclomet, mandipro-amid, oxytetracyclin, silthiofam and N-(6-methoxy-pyridin-3-yl) cyclopropanecarboxylic acid amide;

C) azoles:

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;

imidazoles: cyazofamid, imazalil, pefurazoate, prochloraz, triflumizol;

D) heterocyclic compounds:

pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester;

others: acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a]pyrimidine;

E) Other Active Substances:

guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dicloran, dinobuton, dinocap, nitrothal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorus acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate and sulfur.

Commercial fungicides are most suitably used in accordance with the manufacturer's instructions at the recommended concentrations.

Insecticide(s), Acaricide(s) Nematicide(s):

In at least one embodiment, the biopesticides (i.e., compositions described herein) may optionally comprise one or more insecticides, acaricides, nematicides, or combinations thereof. Alternatively, the one or more insecticides, acaricides, nematicides may be applied either simultaneously or applied sequentially, with the biopesticides disclosed herein. Insecticides useful to the biopesticides described herein will suitably exhibit activity against a broad range of insects including, but not limited to, wireworms, cutworms, grubs, corn rootworm, seed corn maggots, flea beetles, chinch bugs, aphids, leaf beetles, stink bugs, and combinations thereof.

Non-limiting examples of insecticides, acaricides and nematicides that may be useful to the biopesticides disclosed herein include acrinathrin, alpha-cypermethrin, betacyfluthrin, cyhalothrin, cypermethrin, deltamethrin csfenvalcrate, etofenprox, fenpropathrin, fenvalerate, flucythrinat, lambda-cyhalothrin, gamma-cyhalothrin, permethrin, tau-fluvalinate, transfluthrin, zeta-cypermethrin, cyfluthrin, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (Rynaxypyr), Cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, fenamiphos, 4-{[(6-chloropyrid-3-yl)methyl](2,2-difluoroethyl)amino}furan-2(5H)-one, cadusaphos, carbaryl, carbofuran, ethoprophos, thiodicarb, aldicarb, metamidophos, methiocarb, sulfoxaflor and also products based on *Bacillus firmus* (I-1582, BioNeem, Votivo), and combinations thereof.

In a particular embodiment, the biopesticides disclosed herein comprise a nematicide. In a more particular embodiment, the nematicide is a microbial nematicide, more preferably a nematophagous fungus and/or nematophagous bacteria. In a particular embodiment, the microbial nematicide is a nematophagous fungus selected from the group consisting of *Arthrobotrys* spp., *Dactylaria* spp., *Harposporium* spp., *Hirsutella* spp., *Monacrosporium* spp., *Nematoctonus* spp., *Meristacrum* spp., *Myrothecium* spp., *Paecilomyces* spp., *Pasteuria* spp., *Pochonia* spp., *Trichoderma* spp., *Verticillium* spp., and combinations thereof. In still a more particular embodiment, the nematophagous fungus is selected from the group consisting of *Arthrobotrys dactyloides, Arthrobotrys oligospora, Arthrobotrys superb, Arthrobotrys dactyloides, Dactylaria candida, Harposporium anguillulae, Hirsutella rhossiliensis, Hirsutella minnesotensis, Monacrosporium cionopagum, Nematoctonus geogenius, Nematoctonus leiosporus, Meristacrum asterospermum, Myrothecium verrucaria, Paecilomyces lilacinus, Paecilomyces fumosoroseus, Pasteuria penetrans, Pasteuria usgae, Pochonia chlamydopora, Trichoderma harzianum, Verticillium chlamydosporum*, and combinations thereof.

In a more particular embodiment, the microbial nematicide is a nematophagous bacteria selected from the group consisting of *Actinomycetes* spp., *Agrobacterium* spp., *Arthrobacter* spp., *Alcaligenes* spp., *Aureobacterium* spp., *Azobacter* spp., *Beijerinckia* spp., *Burkholderia* spp., *Chromobacterium* spp., *Clavibacter* spp., *Clostridium* spp., *Comomonas* spp., *Corynebacterium* spp., *Curtobacterium* spp., *Desulforibtio* spp., *Enterobacter* spp., *Flavobacterium* spp., *Gluconobacter* spp., *Hydrogenophage* spp., *Klebsiella* spp., *Methylobacterium* spp., *Phyllobacterium* spp., *Phingobacterium* spp., *Photorhabdus* spp., *Serratia* spp. *Stenotrotrophomonas* spp., *Xenorhadbus* spp. *Variovorax* spp., *Streptomyces* spp., *Pseudomonas* spp., *Paenibacillus* spp., and combinations thereof. In still a more particular embodiment, the microbial nematicide is a nematophagous bacteria selected from the group consisting of *Chromobacterium subtsugae, Chromobacterium violaceum, Streptomyces lydicus, Streptomyces violaceusniger*, and combinations thereof. In a particular embodiment, the strain of *Chromobacterium subtsugae* is a strain of *Chromobacterium subtsugae* sp. nov., more particularly, the strain of *Chromobacterium subtsugae* sp. nov. has the deposit accession number NRRL B-30655. In still another particular embodiment, the strain of *Streptomyces* is a strain of *Streptomyces lydicus* WYEC 108, a strain of *Streptomyces violaceusniger* YCED 9, or a combination thereof.

Insect Growth Regulators

In at least one embodiment, the biopesticides (i.e., compositions described herein) may optionally comprise one or more insect growth regulators. Alternatively, the one or more insect growth regulators may be applied either simultaneously or applied sequentially, with the biopesticides disclosed herein. Non-limiting examples of insect growth regulators include pyripoxyfen, ethofenprox, cold-pressed neem oil, S-hydroprene, chitin synthesis inhibitors, juvenile hormone analogs (e.g. methoprene) and combinations thereof.

Polymer(s):

In at least one embodiment, the biopesticides (i.e., compositions described herein) may optionally comprise one or more polymers. Alternatively, the one or more polymers may be applied either simultaneously or applied sequentially, with the biopesticides disclosed herein. Non-limiting uses of polymers in the agricultural industry include agrochemical delivery (e.g., use as an aqueous dispersant), heavy metal removal, water retention and/or water delivery, and combinations thereof. Pouci, et al., Am. J. Agri. & Biol. Sci., 3(1):299-314 (2008). In one embodiment, the one or more polymers is a natural polymer (e.g., agar, starch, alginate, pectin, cellulose, etc.), a synthetic polymer, a biodegradable polymer (e.g., polycaprolactone, polylactide, poly (vinyl alcohol), etc.), or a combination thereof.

For a non-limiting list of polymers useful for the compositions described herein, see Pouci, et al., Am. J. Agri. & Biol. Sci., 3(1):299-314 (2008). In one embodiment, the compositions described herein comprise cellulose, cellulose derivatives, methylcellulose, methylcellulose derivatives, starch, agar, alginate, pectin, polyvinylpyrrolidone, polymeric surfactants, and combinations thereof.

In a particular embodiment, the biopesticide may comprise one or more polymeric surfactants. Polymeric surfactants that may be suitable for the biopesticides described herein may include one or more nonionic polymeric surfactants, anionic polymeric surfactants, amphoteric polymeric surfactants, cationic polymeric surfactants, and combinations thereof. Particularly useful polymeric surfactants to the biopesticides described herein are polymeric surfactants that are capable of functioning as an aqueous dispersant.

Nonionic Polymeric Surfactants:

Non-limiting examples of nonionic polymeric surfactants include polyalkylene oxide block copolymers, butyl block copolymers, nonionic block copolymers, acrylic copolymer solutions, nonionic random polymeric polymers, polyoxyethylene polyarl phenols, and nonionic polymeric dispersants. Commercially available nonionic polymeric surfactants include, but are not limited to, Atlas® G-5000, Atlas®

G-5002L, Atlox® 4894, Atlox® 4912, Atlox® 4912-SF, Atlox® 4913, Atlox® 4914, Cresplus® DP, Hypermer® B206, Hypermer® B210, Hypermer® B246SF, Zyphrym® PD2206, Zyphrym® PD3315, and Zyphrym® PD7000.

In a particular embodiment, the biopesticide comprises one or more nonionic polymeric surfactants selected from polyalkylene oxide block copolymers, butyl block copolymers, nonionic block copolymers, acrylic copolymer solutions, nonionic random polymeric polymers, polyoxyethylene polyarl phenols, nonionic polymeric dispersants, and combinations thereof. In a more particular embodiment, the biopesticide comprises one or more nonionic polymeric surfactants selected from Atlas® G-5000, Atlas® G-5002L, Atlox® 4894, Atlox® 4912, Atlox® 4912-SF, Atlox® 4913, Atlox® 4914, Cresplus® DP, Hypermer® B206, Hypermer® B210, Hypermer® B246SF, Zyphrym® PD2206, Zyphrym® PD3315, Zyphrym® PD7000, and combinations thereof.

Anionic Polymeric Surfactants:

Non-limiting examples of anionic polymeric surfactants include styrene acrylic polymers, modified styrene acrylic polymers, and anionic polymeric dispersants. Commercially available anionic polymeric surfactants include, but are not limited to, Atlox® Metasperse 100L, Atlox® Metasperse 500L, Atlox® Metasperse 550S, and Atlox® LP-1. In an embodiment, the biopesticide comprises one or more anionic surfactants.

In a particular embodiment, the biopesticide comprises one or more anionic polymeric surfactants selected from styrene acrylic polymers, modified styrene acrylic polymers, anionic polymeric dispersants, and combinations thereof. In a more particular embodiment, the biopesticide comprises one or more anionic polymeric surfactants selected from Atlox® Metasperse 100L, Atlox® Metasperse 500L, Atlox® Metasperse 550S, Atlox® LP-1 and combinations thereof.

In yet another particular embodiment, the biopesticide comprises an anionic polymeric surfactant, wherein the anionic polymeric surfactant comprises one or more modified styrene acrylic polymers. In another particular embodiment, the biopesticide comprises one or more modified styrene acrylic polymers selected from Atlox® Metasperse 500L, Atlox® Metasperse 550S, and combinations thereof. In a particular embodiment the biopesticide comprises Atlox® Metasperse 500L. In another particular embodiment the biopesticide comprises Atlox® Metasperse 550S. In still yet another particular embodiment the biopesticide comprises a mixture of Atlox® Metasperse 500L and Atlox® Metasperse 550S.

Polymeric Amphoteric Surfactants:

Polymeric amphoteric surfactants suitable for the biopesticides described herein include, but are not limited to, polymeric amphoteric dispersants. A commercially available polymeric amphoteric dispersant includes, but is not limited to, Atlox® 4915. In an embodiment, the biopesticide comprises one or more polymeric amphoteric dispersants. In a particular embodiment, the biopesticide comprises Atlox® 4915.

Cationic Polymeric Surfactants:

Cationic polymeric surfactants suitable for the biopesticides described herein include, but are not limited to, polyester/polyamine condensation polymers. A commercially available cationic polymeric surfactant includes Hypermer® KD-1. In an embodiment, the biopesticide comprises one or more polyester/polyamine condensation polymers. In a particular embodiment, the biopesticide comprises Hypermer® KD-1.

Wetting Agent(s):

In at least one embodiment, the biopesticides (i.e., compositions described herein) may optionally comprise one or more wetting agents. Alternatively, the one or more wetting agents may be applied either simultaneously or applied sequentially, with the biopesticides disclosed herein. Wetting agents are commonly used on soils, particularly hydrophobic soils, to improve the infiltration and/or penetration of water into a soil. The wetting agent may be an adjuvant, oil, surfactant, buffer, acidifier, or combination thereof. In an embodiment, the wetting agent is a surfactant. In an embodiment, the wetting agent is one or more nonionic surfactants, one or more anionic surfactants, or a combination thereof. In yet another embodiment, the wetting agent is one or more nonionic surfactants.

Anti-Freezing Agent(s):

In at least one embodiment, the biopesticides (i.e., compositions described herein) may optionally comprise one or more anti-freezing agents. Alternatively, the one or more anti-freezing agents may be applied either simultaneously or applied sequentially, with the biopesticides disclosed herein. In one embodiment, the compositions described herein may further comprise one or more anti-freezing agents. Non-limiting examples of anti-freezing agents include ethylene glycol, propylene glycol, urea, glycerin, and combinations thereof.

Preservatives

In at least one embodiment, the biopesticides (i.e., compositions described herein) may optionally comprise one or more preservatives. Alternatively, the one or more preservatives may be applied either simultaneously or applied sequentially, with the biopesticides disclosed herein. As used herein, the term "preservative" includes a biocide (i.e., a bacteriostats or a bactericides). Non-limiting examples of biocides include the following:

Bactericides:

As used herein, a bactericide is an agent that kills bacteria. A bactericide may be a disinfectant, antiseptic or antibiotic.

Non-limiting examples of a bactericidal disinfectant may be:

active chlorine (i.e., hypochlorites, chloramines, dichloroisocyanurate and trichloroisocyanurate, wet chlorine, chlorine dioxide, etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds, such as chlorhexidine, glucoprotamine, octenidine dihydrochloride, etc.), strong oxidizers, such as ozone and permanganate solutions;

heavy metals and their salts, such as colloidal silver, silver nitrate, mercury chloride, phenylmercury salts, copper sulfate, copper oxide-chloride, etc. Heavy metals and their salts are the most toxic, and environment-hazardous bactericides and therefore, their use is strongly oppressed or eliminated; further, also properly concentrated strong acids (phosphoric, nitric, sulfuric, amidosulfuric, toluenesulfonic acids) and alkalis (sodium, potassium, calcium hydroxides), such as of pH<1 or >13, particularly under elevated temperature (above 60° C.), kills bacteria.

Non-limiting examples of a bactericidal antiseptic may be:

properly diluted chlorine preparations (e.g., Daquin's solution, 0.5% sodium or potassium hypochlorite solution, pH-adjusted to pH 7-8, or 0.5-1% solution of sodium benzenesulfochloramide (chloramine B)), some iodine preparations, such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid, some phenolic compounds, such as hexachlorophene, triclosan and Dibromol, and cation-active compounds, such as 0.05-0.5% benzalkonium, 0.5-4% chlorhexidine, 0.1-2% octenidine solutions.

Non-limiting examples of a bactericidal antibiotic may be penicillin, cephalosporins, and aminoglycosidic antibiotics.

Other bactericidal antibiotics include the fluoroquinolones, nitrofurans, vancomycin, monobactams, co-trimoxazole, and metronidazole.

Preferred bactericides are:
Halogen containing compounds such as:
  Bronopol—active 2-bromo-2-nitro-1,3-propanadiol
  Dowicil 75—active 1-(3-chloroallyl)-3,5,7-triaza-1-azoniaadamantane chloride
  DBNPA—active dibromonitrilopropionamide
OrganoSulfurs—includes Isothaizolones such as:
  Proxel (Nipacide)—active 1,2-benzisothiazolin-3-one
  Kathon—active 5-chloro-2-methyl-4-isosthiazolin-3-one, 2-methyl-4-isosthiazolin-3-one
Nitrogen containing compounds such as:
  Germall II (Diazolidinyl urea)
  Tris nitro (tris(hydroxymethyl)nitromethane)
Phenolics such as:
  Dowicide (sodium o-phenylphenate)
  Preventol D2® (benzyl-hemiformal)
Inorganics such as:
  copper arsenates
  cuprous oxide
Organometallics such as:
  compounds of arsenic, copper, mercury
Quaternary ammonium compounds.
  Bacteriostats:

As used herein, a bacteriostat is an agent, usually chemical, that prevents the growth of bacteria but that does not necessarily kill them or their spores. Upon removal of the bacteriostat, the bacteria usually start to grow again.

Non-limiting examples of bacteriostats include sodium azide and thimerosol.
Methods In another aspect, methods of using the biopestices (i.e., compositions disclosed herein) to control one or more pests are disclosed. In a particular embodiment, the method comprises controlling one or more plant pests. Non-limiting examples of plant pests include:

Hemiptera Harmful Insects:

Planthoppers (Delphacidae) such as small brown planthopper (*Laodelphax striatellus*), brown rice planthopper (*Nilaparvata lugens*), white-backed rice planthopper (*Sogatella furcifera*) and the like; leafhoppers (Deltocephalidae) such as green rice leafhopper (*Nephotettix cincticeps*), green rice leafhopper (*Nephotettix virescens*) and the like; aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*) and the like; stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), tarnished plant bug (*Lyus lineolarxs*) and the like; whiteflies (Aleyrodidae) such as greenhouse whitefly (*Trialeurodes vaporariorum*), sweetpotato whitefly (*Bemisia tabaci*), silverleaf whitefly (*Bemisia argentifolii*) and the like; scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*) and the like; lace bugs (Tingidae); psyllids (Psyllidae); etc.

Lepidoptera Harmful Insects:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia fumacalis*), European corn borer (*Ostrinia nubilaris*), cabbage webworm (*Hellula undalis*), bluegrass webworm (*Pediasia teterrellus*) and the like; owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., *Helicoverpa* spp. and the like; white butterflies (Pieridae) such as common white (*Pieris rapae*) and the like; tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* spp.), oriental tea tortrix (*Homona magnanima*), apple tortrix (*Archips fuscocupreanus*), codling moth (*Cydia pomonella*) and the like; leafblotch miners (Gracillariidae) such as tea leafroller (*Caloptilia theivora*), apple leafminer (*Phyllonorycter ringoneella*) and the like; Carposinidae such as peach fruit moth (*Carposina niponensis*) and the like; lyonetiid moths (Lyonetiidae) such as *Lyonetia* spp. and the like; tussock moths (Lymantriidae) such as *Lymantria* spp., *Euproctis* spp. and the like; yponomeutid moths (Yponomeutidae) such as diamondback (*Plutella xylostella*) and the like; gelechiid moths (Gelechiidae) such as pink bollworm (*Pectinophora gossypiella*), potato tubeworm (*Phthorimaea operculella*) and the like; tiger moths and allies (Arctiidae) such as fall webworm (*Hyphantria cunea*) and the like; tineid moths (Tineidae) such as casemaking clothes moth (*Tinea translucens*), webbing clothes moth (*Tineola bisselliella*) and the like; etc.

Thysanoptera Harmful Insects:

Thrips (Thripidae) such as western flower thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), tobacco thrips (*Frankliniella fusca*) and the like, etc.;

Diptera Harmful Insects:

House flies (*Musca domestica*), common house mosquito (*Culex popiens pallens*), horsefly (*Tabanus trigonus*), onion fly (*Hylemya antiqua*), seedcorn maggot (*Hylemya platura*), asian tiger mosquito (*Anopheles sinensis*); leafminer flies (Agromyzidae) such as rice leafminer (*Agromyza oryzae*), little rice leafminer (*Hydrellia griseola*), rice stemmaggot (*Chlorops oryzae*), legume leafminer (*Liriomyza trifolii*) and the like; melon fly (*Dacus cucurbitae*), Meditteranean fruit fly (*Ceratitis capitata*), etc.;

Coleoptera Harmful Insects:

Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popxllia japonica*), cupreous chafer (*Anomala cuprea*), Corn root worms (*Diabrotica* spp.), Colorado potato beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder-post beetle (*Lyctus brunneus*), white-spotted longicorn beetle (*Anoplophora malasiaca*), pine shoot beetle (*Tomicus piniperda*), etc.;

Orthoptera Harmful Insects:

Asiatic locust (*Locusta migratoria*), African mole cricket (*Gryllotalpa africana*), rice grasshopper (*Oxya yezoensis*), rice grasshopper (*Oxya japonica*), etc.;

Hymenoptera Harmful Insects:

Cabbage sawfly (*Athalia rosae*), leaf-cutting ant (*Acromyrmex* spp.), fire ant (*Solenopsis* spp.), etc.;

Blattodea Harmful Insects:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*), etc.

Particular examples of the above-described harmful arthropods include aphids (Aphididae), Thrips (Thripidae), leafminer flies (Agromyzidae), horsehair worms (*Paragordius tricuspidatus*), Colorado potato beetle (*Leptinotarsa decemlineata*), Japanese beetle (*Popillia japonica*), cupreous chafer (*Anomala cuprea*), boll weevil (*Anthonomus grandis*), rice water weevil (*Lissorhoptrus oryzophilus*), tobacco thrips (*Frankliniella fusca*), Corn root worms (*Diabrotica* spp.), diamondback (*Plutella xylostella*), cabbageworms, soybean pod borer (*Leguminivora glycinivorella*), and the like.

In a particular embodiment, the method includes controlling one or more plant pests with a biopesticide comprising contacting a plant pest with one or more of the biopesticides (i.e., compositions) described herein. The contacting step can be performed by any method known in the art (e.g., spraying, dusting, etc.). In one embodiment, the contacting step is repeated (e.g., more than once, as in the contacting step is repeated twice, three times, four times, five times, six times, seven times, eight times, nine times, ten times, etc.).

In another aspect, a method for controlling one or more pest with a biopesticide comprising contacting a plant or plant part with one or more of the biopesticides described herein. Without being bound by theory, it is believed the one or more pests, e.g., plant pests, will come into contact with the biopesticides when in contact with a treated plant or plant part. In an embodiment, the contacting step can be performed by any method known in the art (including both foliar and non-foliar applications). Non-limiting examples of contacting the plant or plant part include spraying the plant or plant part, drenching the plant or plant part, dripping onto the plant or plant part, dusting the plant or plant part, and/or coating a seed with one or more of the biopesticides described herein. In one embodiment, the contacting step is repeated (e.g., more than once, as in the treating step is repeated twice, three times, four times, five times, six times, seven times, eight times, nine times, ten times, etc.). The contacting step can occur at any time during the growth of the plant or plant part. In one embodiment, contacting a plant or plant part with one or more of the biopesticides described herein occurs before the plant or plant part begins to grow. In another embodiment, contacting a plant or plant part with one or more of the biopesticides described herein occurs after the plant or plant part has started to grow.

In another aspect, a method for controlling one or more pest with a biopesticide comprising treating a soil with one or more of the biopesticides described herein. Without being bound by theory, it is believed the one or more pests, e.g., plant pests, will come into contact with the biopesticides when in contact with a treated soil. In an embodiment, the treating step can be performed by any method known in the art (including both foliar and non-foliar applications). Non-limiting examples of treating the soil include spraying the soil, drenching the soil, dripping onto the soil, and/or dusting the soil with one or more of the biopesticides described herein. In one embodiment, the treating step is repeated (e.g., more than once, as in the treating step is repeated twice, three times, four times, five times, six times, seven times, eight times, nine times, ten times, etc.). The treating step can occur at any time during the growth of the plant or plant part. In one embodiment, the treating step occurs before the plant or plant part begins to grow. In another embodiment, the treating step occurs after the plant or plant part has started to grow.

In another embodiment, the method further comprises the step of planting a plant or plant part. The planting step can occur before, after or during the treatment of the solid with one or more of the biopesticides described herein. In one embodiment, the planting step occurs before the soil is treated with one or more of the biopesticides described herein. In another embodiment, the planting step occurs during the treatment of the soil with one or more of the biopesticides described herein (e.g., the planting step occurs substantially simultaneous with the treating step, etc.). In still another embodiment, the planting step occurs after the soil is treated with one or more of the biopesticides described herein.

In another embodiment, the method further comprises the step of subjecting the pest, the plant or plant part, and/or the soil to one or more of the optional ingredients described herein. The pest, the plant or plant part, and/or the soil can be subjected to one or more of the optional ingredients as part of a biopesticides described herein or independently from the one or more biopesticides (i.e., compositions) described herein.

In one embodiment, the pest, the plant or plant part, and/or the soil is subjected to one or more of the optional ingredients as part of the biopesticides (i.e., compositions) described herein. In another embodiment, the pest, the plant or plant part, and/or the soil is subjected to one or more of the optional ingredients independently from the one or more biopesticides described herein.

In one embodiment, subjecting one or more of the optional ingredients to the pest, the plant or plant part, and/or the soil occurs before, during, after, or simultaneously with the contacting and/or treating steps. In one embodiment, subjecting one or more of the optional ingredients to the pest, the plant or plant part, and/or the soil occurs before the contacting and/or treating steps. In another embodiment, subjecting one or more of the optional ingredients to the pest, the plant or plant part, and/or the soil occurs during the contacting and/or treating steps. In still another embodiment, subjecting one or more of the optional ingredients to the pest, the plant or plant part, and/or the soil occurs after the contacting and/or treating steps. In yet another embodiment, subjecting one or more of the optional ingredients to the pest, the plant or plant part, and/or the soil occurs simultaneously with the contacting and/or treating steps.

Seed Coatings

In another aspect, seeds are coated with one or more of the biopesticides (i.e., compositions) described herein. In one embodiment, seeds may be treated with composition described herein in several ways but preferably via spraying or dripping. Spray and drip treatment may be conducted by formulating biopesticides described herein and spraying or dripping the biopesticides onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed. Systems and apparati for performing these processes are commercially available from numerous suppliers, e.g., Bayer CropScience (Gustafson).

In another embodiment, the treatment entails coating seeds. One such process involves coating the inside wall of a round container with the biopesticides described herein, adding seeds, then rotating the container to cause the seeds to contact the wall and the biopesticides, a process known in the art as "container coating". Seeds can be coated by combinations of coating methods. Soaking typically entails using liquid forms of the biopesticides described. For example, seeds can be soaked for about 1 minute to about 24 hours (e.g., for at least 1 min, 5 min, 10 min, 20 min, 40 min, 80 min, 3 hr, 6 hr, 12 hr, 24 hr).

Application Rates and Dilutions

The biopesticides described herein may be applied at varying concentrations to perform any of the methods disclosed or to any of the seed coatings or methods of coating seeds described herein. In an embodiment, the biopesticides are diluted with water. In a particular embodiment the biopesticide is diluted with water at a rate of 0.01 to 5.00 g of biopesticide to 95.00 g to 99.99 g of water In a particular embodiment, the biopesticide is diluted with water at a rate of 5.00 g of biopesticide to 95.00 g of water. In another particular embodiment, the biopesticide is diluted with water at a rate of 4.00 g of biopesticide to 96.00 g of water. In still another particular embodiment, the biopesticide is diluted with water at a rate of 3.00 g of biopesticide to 97.00 g of water. In yet another particular embodiment, the biopesticide is diluted with water at a rate of 2.00 g of biopesticide to 98.00 g of water. In still yet another particular embodiment, the biopesticide is diluted with water at a rate of 1.00 g of biopesticide to 99.00 g of water. In yet still another particular embodiment, the biopesticide is diluted with water at a rate of 0.90 g of biopesticide to 99.10 g of water. In another particular embodiment, the biopesticide is diluted with water at a rate of 0.80 g of biopesticide to 99.20 g of water. In still another particular embodiment, the biopesticide is diluted with water at a rate of 0.70 g of biopesticide to 99.30 g of water. In yet another particular embodiment, the biopesticide is diluted with water at a rate of 0.60 g of biopesticide to 99.40 g of water. In still yet another particular embodiment, the biopesticide is diluted with water at a rate of 0.50 g of biopesticide to 99.50 g of water. In yet still another embodiment, the biopesticide is diluted with water at a rate of 0.40 g of biopesticide to 99.60 g of water. In another particular embodiment, the biopesticide is diluted with water at a rate of 0.35 g of biopesticide to 99.65 g of water. In still another particular embodiment, the biopesticide is diluted with water at a rate of 0.30 g of biopesticide to 99.70 g of water. In yet another particular embodiment, the biopesticide is diluted with water at a rate of 0.25 g of biopesticide to 99.75 g of water. In still yet another particular embodiment, the biopesticide is diluted with water at a rate of 0.20 g of biopesticide to 99.80 g of water. In yet still another particular embodiment, the biopesticide is diluted with water at a rate of 0.15 g of biopesticide to 99.85 g of water. In another particular embodiment, the biopesticide is diluted with water at a rate of 0.10 g of biopesticide to 99.90 g of water. In still another particular embodiment, the biopesticide is diluted with water at a rate of 0.05 g of biopesticide to 99.95 g of water. In yet another particular embodiment, the biopesticide is diluted with water at a rate of 0.01 g of biopesticide to 99.99 g of water.

The invention will now be described in terms of the following non-limiting examples.

EXAMPLES

The following examples are provided for illustrative purposes and are not intended to limit the scope of the invention as claimed herein. Any variations in the exemplified examples which occur to the skilled artisan are intended to fall within the scope of the present invention.

Example 1. Biopesticide Formulations

Materials & Methods:
Paraffinic Oil:
  SunSpray® 6N
Fumed Silica:
  Cab-O-Sil® M-5
  Cab-O-Sil® TS-720
Polyoxyethylene (40) Sorbitol Hexaoleate:
  Cirrasol® G-1086
Sorbitan Monostearate:
  Span® 60
Sorbitan Monooleate:
  Span® 80
Modified Styrene Acrylic Polymer:
  Metasperse® 550S
Fungal Pesticide (Spores):
  Spores of *Metarhizium anisopliae* (also referred to as *Metarhizium brunneum*)
Biopesticide Compositions:
  The following biopesticides (i.e., compositions) were prepared as follows. Sunspray 6N oil was combined with Cab-O-Sil M-5 and blended for 3 minutes on high-speed using a Waring Commercial Laboratory Blender. The resulting liquid was divided by pouring 100 mL into separate Ball mason jar carafes. The remaining components were promptly added and blended for 2 minutes. Each was poured into 250 bottles. Technical grade MET52 spore powder was added to each sample, and each sample was shaken on a Burrerell Wrist-Action Shaker for 10 minutes.

In each biopesticide (i.e., composition), the quantity of each ingredient is given in weight percentage (wt. %) and reflected in Table 2.

TABLE 2

Biopesticide compositions

| Compositions | % SunSpray 6N | % Cab-O-Sil M5 | % Cab-O-Sil TS-720 | % Cirrasol G-1086 | % Span 60 | % Span 80 | % Metasperse 550S | % Met 52 |
|---|---|---|---|---|---|---|---|---|
| Composition 1 | 56.00 | 3.00 | 0.00 | 27.75 | 0.00 | 2.25 | 0.00 | 11.00 |
| Composition 2 | 75.50 | 1.00 | 0.00 | 12.50 | 0.00 | 0.00 | 0.00 | 11.00 |
| Composition 3 | 70.50 | 1.00 | 0.00 | 12.50 | 0.00 | 0.00 | 5.00 | 11.00 |
| Composition 4 | 75.50 | 1.00 | 0.00 | 12.34 | 0.16 | 0.00 | 0.00 | 11.00 |
| Composition 5 | 70.50 | 1.00 | 0.00 | 12.34 | 0.16 | 0.00 | 5.00 | 11.00 |
| Composition 6 | 80.50 | 1.00 | 0.00 | 7.402 | 0.098 | 0.00 | 0.00 | 11.00 |
| Composition 7 | 75.50 | 1.00 | 0.00 | 7.402 | 0.098 | 0.00 | 5.00 | 11.00 |
| Composition 8 | 80.50 | 1.00 | 0.00 | 7.50 | 0.00 | 0.00 | 0.00 | 11.00 |
| Composition 9 | 75.50 | 1.00 | 0.00 | 7.50 | 0.00 | 0.00 | 5.00 | 11.00 |
| Composition 10 | 78.00 | 1.00 | 0.00 | 10.00 | 0.00 | 0.00 | 0.00 | 11.00 |
| Composition 11 | 78.00 | 1.00 | 0.00 | 9.50 | 0.50 | 0.00 | 0.00 | 11.00 |
| Composition 12 | 78.00 | 1.00 | 0.00 | 9.00 | 1.00 | 0.00 | 0.00 | 11.00 |
| Composition 13 | 78.00 | 1.00 | 0.00 | 8.50 | 1.50 | 0.00 | 0.00 | 11.00 |
| Composition 14 | 73.00 | 1.00 | 0.00 | 10.00 | 0.00 | 0.00 | 5.00 | 11.00 |
| Composition 15 | 73.00 | 1.00 | 0.00 | 9.50 | 0.50 | 0.00 | 5.00 | 11.00 |
| Composition 16 | 73.00 | 1.00 | 0.00 | 9.00 | 1.00 | 0.00 | 5.00 | 11.00 |
| Composition 17 | 73.00 | 1.00 | 0.00 | 8.50 | 1.50 | 0.00 | 5.00 | 11.00 |
| Composition 18 | 68.00 | 1.00 | 0.00 | 10.00 | 0.00 | 0.00 | 10.00 | 11.00 |
| Composition 19 | 68.00 | 1.00 | 0.00 | 9.50 | 0.50 | 0.00 | 10.00 | 11.00 |
| Composition 20 | 68.00 | 1.00 | 0.00 | 9.00 | 1.00 | 0.00 | 10.00 | 11.00 |
| Composition 21 | 68.00 | 1.00 | 0.00 | 8.50 | 1.50 | 0.00 | 10.00 | 11.00 |
| Composition 22 | 73.00 | 1.00 | 0.00 | 9.00 | 0.00 | 1.00 | 5.00 | 11.00 |
| Composition 23 | 68.00 | 1.00 | 0.00 | 14.25 | 0.00 | 0.75 | 5.00 | 11.00 |
| Composition 24 | 68.00 | 1.00 | 0.00 | 12.75 | 0.00 | 2.25 | 5.00 | 11.00 |
| Composition 25 | 63.00 | 1.00 | 0.00 | 19.00 | 0.00 | 1.00 | 5.00 | 11.00 |
| Composition 26 | 63.00 | 1.00 | 0.00 | 17.00 | 0.00 | 3.00 | 5.00 | 11.00 |
| Composition 27 | 68.00 | 1.00 | 0.00 | 8.50 | 0.00 | 1.50 | 10.00 | 11.00 |
| Composition 28 | 73.00 | 1.00 | 0.00 | 8.50 | 0.00 | 1.50 | 5.00 | 11.00 |
| Composition 29 | 61.00 | 1.00 | 2.00 | 17.00 | 0.00 | 3.00 | 5.00 | 11.00 |
| Composition 30 | 68.00 | 1.00 | 0.00 | 18.00 | 0.00 | 2.00 | 0.00 | 11.00 |
| Composition 31 | 68.00 | 1.00 | 0.00 | 19.00 | 0.00 | 1.00 | 0.00 | 11.00 |
| Composition 32 | 63.00 | 1.00 | 0.00 | 23.75 | 0.00 | 1.25 | 0.00 | 11.00 |
| Composition 33 | 58.00 | 1.00 | 0.00 | 28.50 | 0.00 | 1.50 | 0.00 | 11.00 |
| Composition 34 | 63.00 | 1.00 | 0.00 | 22.50 | 0.00 | 2.50 | 0.00 | 11.00 |
| Composition 35 | 58.00 | 1.00 | 0.00 | 27.00 | 0.00 | 3.00 | 0.00 | 11.00 |
| Composition 36 | 66.00 | 3.00 | 0.00 | 18.00 | 0.00 | 2.00 | 0.00 | 11.00 |
| Composition 37 | 64.00 | 5.00 | 0.00 | 18.00 | 0.00 | 2.00 | 0.00 | 11.00 |
| Composition 38 | 61.00 | 3.00 | 0.00 | 22.50 | 0.00 | 2.50 | 0.00 | 11.00 |
| Composition 39 | 59.00 | 5.00 | 0.00 | 22.50 | 0.00 | 2.50 | 0.00 | 11.00 |
| Composition 40 | 61.00 | 3.00 | 0.00 | 23.125 | 0.00 | 1.875 | 0.00 | 11.00 |

Values provided in wt. %.

Example 2. Span™ 60 Addition and Phytotoxicity

Formulations with and without Span™ 60 were prepared as described below and then tested for phytotoxiciity. The objective was to determine whether phytoxicity could be minimized while retaining the emulsion properties of the formulation, and minimizing deposition of residues of oil and spores on plastic surfaces.

The formulations given below in Table 3 were prepared as follows: SunSpray® 6N oil was combined with Cab-O-Sil® M-5 and blended for 3 minutes on high-speed using a Waring Commercial Laboratory Blender. The resulting liquid was divided by pouring 100 mL into separate Ball mason jar carafes. The remaining components were promptly added and blended for 2 minutes. Each was poured into 250 bottles. Technical grade MET52 spore powder was added to each sample, and each sample was shaken on a Burrerell Wrist-Action Shaker for 10 minutes. Finally, each sample was divided into two 50 mL LDPE plastic bottles in preparation for phytotoxicity evaluation.

Prior to phytotoxicity evaluation, formulations were diluted to either 0.8% or 1.6% weight to weight in glass Erlenmyer flasks with water having the following properties (K 5.21 mg/L; Ca 30.39 mg/L; Mg 19.41 mg/L; Na 1.5 mg/L; $PO_4$ 0.38 mg/L; $SO_4$ 12.78 mg/L; Cl 2.1 mg/L; $HCO_3$ 176 mg/L; $CO_3$ ND; $NH_4$—N 0.5 mg/L; $NO_3$—N 0.2 mg/L; pH 7.2; EC soluble salts 0.32 mg/L; total alkalinity $CaCO_3$ 144.27 mg/L; Fe ND; Mn ND; B 0.03 mg/L; Cu 0.01 mg/L; Zn ND; Mo 0.01 mg/L; Al 0.05 mg/L). Approximately ½ of the measured amount of water was added to the flask. Then the required amount of formulation was added to the flask. After this, the remaining amount of measured water was added to the flask and shaken. These aqueous suspensions were used within 5 minutes of preparation.

A mist nozzle was used to treat either 3 week old Maverick Red geraniums or 4 week old Wisconsin cucumbers. Each plant was replicated 6 times. Applications were repeated after 4 days and a final evaluation for phytotoxicity was made after 7 days form the first application. Phytotoxicity was rated on a 1-10 scale where 10 represented the most severe damage observed. Geraniums exhibited phytotoxicity in the form of necrotic lesions and cucumbers exhibited phytotoxicity in the form of marginal burn and epinasty. Differences among treatments were compared using a 5% Duncan's new mean separation. Mean comparisons only performed when global F-statistics is significant at pre-specified significant level (p=0.1). The data in Table 3 is a subset of a trial that included 29 treatments.

TABLE 3

Comparison of phytotoxicity among different formulations.

| Experimental Formulation | Sunspray 6N Oil | Cab-O-Sil M-5 | Cirrasol G-1086 | Span 60 | % of NIS as Span | Geranium at 1.6% formulation (w/w) | Cucumber at 0.8% formulation (w/w) | Cucumber at 1.6% formulation (w/w) |
|---|---|---|---|---|---|---|---|---|
| A without | 75.5 | 1 | 12.5 | 0 | 0 | 2.7 de | 4.0 cd | 5.8 b |
| A with | 75.5 | 1 | 12.34 | 0.16 | 1.3 | 1.6 fgh | 2.5 e-j | 4.5 c |
| Difference for A | | | | | | −1.4 | −1.5 | −1.3 |
| C without | 80.5 | 1 | 7.5 | 0 | 0 | 2.0 efg | 1.9 g-l | 3.6 cde |
| C with | 80.5 | 1 | 7.403 | 0.098 | 1.3 | 1.1 ghi | 1.8 h-l | 2.1 g-k |
| Difference for C | | | | | | −0.9 | −0.1 | −1.5 |
| LSD (P = 0.10) | | | | | | 0.68 | | 0.76 |
| Standard Deviation | | | | | | 0.77 | | 0.64 |
| CV | | | | | | 61.62 | | 23.45 |
| Bartlett's X2 | | | | | | 96.003 | | 35.758 |
| P (Bartlett's X2) | | | | | | 0.001 | | 0.058 |
| Treatment F | | | | | | 33.258 | | 39.916 |
| Treatment Prob(F) | | | | | | 0.0001 | | 0.0001 |

*Means followed by the same letter among rows and columns for the two rates of the same plant type do not significantly differ (P = 0.1, Student-Newman-Keuls)
**All formulations contained 11% *Metarhizium anisopliae* spores by weight.

These studies show a reduction in phytotoxicity of the formulations when Span™ 60 is used as a component of the surfactant system. In 11 of 16 comparisons, the addition of Span™ 60 reduced phytotoxicity. The conclusion is that addition of Span™ 60 to the formulation reduced phytotoxicity.

Example 3. Variation of Span™ 60 Concentrations

Formulations with increasing concentrations of Span™ 60, as described in Table 4, were prepared as described in Example 2.

Phytotoxicity testing on cucumber was conducted and data were analyzed as described in Example 2 with the exception that final injury ratings were made at 8 days after initial application rather than 7. The data in Table 4 is a subset of data from a trial that included 29 treatments.

TABLE 4

Comparison of phytotoxicity to cucumber among different formulations.

|

TABLE 4-continued

Comparison of phytotoxicity to cucumber among different formulations.

| Experimental Formulation | Sunspray 6N Oil | Cab-O-Sil M-5 | Cirrasol G-1086 | Span 60 | % of NIS as Span | Atlox Metasperse 550S | Cucumber at 0.8% formulation (w/w) | Cucumber at 1.6% formulation (w/w) |
|---|---|---|---|---|---|---|---|---|
| G without | 68 | 1 | 10 | 0 | 0 | 10 | 5.05 c-g | 7.1 b-f |
| G1 with 5% | 68 | 1 | 9.5 | 0.5 | 5 | 10 | 3.75 d-h | 3.6 b-e |
| G2 with 10% | 68 | 1 | 9 | 1 | 10 | 10 | 1.65 e-i | 1.6 e-h |
| G3 with 15% | 68 | 1 | 8.5 | 1.5 | 15 | 10 | 1.7 f-i | 1.7 ghi |
| Difference for G1 | | | | | | | −1.3 | −3.5 |
| Difference for G2 | | | | | | | −3.4 | −5.5 |
| Difference for G3 | | | | | | | −3.35 | −5.4* |

*All formulations contained 11% *Metarhizium anisopliae* spores by weight.
**Expressed as percent of surfactant made up by Span 60.

The data show that increasing Span™ 60 content relative to the total anionic surfactant content, decreases phytotoxicity. In each of the tested formulations, there was a trend of decreasing phytotoxicity as levels of Span™ 60 were increased.

Example 4. Comparison of Span™ 60 with Span™ 80

Formulations containing Span™ 60 and Span™ 80, as described in Table 5 were prepared as described in Example 2. Phytotoxicity testing on geranium and cucumber was conducted and data analyzed as described in Example 2 with the exception that final injury ratings were made at 8 days after initial application rather than 7. The data in Table 5 are a subset of a trial that included 29 treatments.

TABLE 5

Comparison of phytotoxicity to geranium and cucumber among different formulations.

| Experimental Formulation | Sunspray 6N Oil | Cab-O-Sil M-5 | Cirrasol G-1086 | Span 60 | Span 80 | % of NIS as Span | Atlox Metasperse 550S | Geranium at 0.8% formulation (w/w) | Geranium at 1.6% formulation (w/w) | Cucumber at 0.8% formulation (w/w) | Cucumber at 1.6% formulation (w/w) |
|---|---|---|---|---|---|---|---|---|---|---|---|
| Control | 0 | 0 | 0 | 0 | 0 | 0 | 0 | 0 c | 0 c | 0 c | 0 c |
| H | 78 | 1 | 10 | 0 | | 0 | 0 | 0 c | 0.67 bc | 0.17 bc | 0.83 bc |
| I | 73 | 1 | 9 | 1 | | 10 | 5 | 0.33 bc | 0.33 bc | 0.17 bc | 0.5 bc |
| J | 73 | 1 | 9 | 0 | 1 | 10 | 5 | 0 c | 0 c | 0.83 bc | 1.5 abc |
| K | 68 | 1 | 14.25 | 0 | 0.75 | 5 | 5 | 0.17 c | 0.5 bc | 1 bc | 0.33 bc |
| L | 68 | 1 | 12.75 | 0 | 2.25 | 15 | 5 | 0 c | 0.17 c | 0.5 bc | 0.5 bc |
| M | 63 | 1 | 19 | 0 | 1 | 5 | 5 | 0.17 c | 0.17 c | 1.33 abc | 1.33 abc |
| N | 63 | 1 | 17 | 0 | 3 | 15 | 5 | 0 c | 0 c | 1.67 ab | 0.5 bc |

* All formulations contained 11% *Metarhizium anisopliae* spores by weight.

The data in Table 5 demonstrates that it was possible to bridge from Span™ 60 to Span™ 80 and increase from 5% to 20% of total surfactant while maintaining the percentage of Span™ 80 in the formulation and still maintain low phytotoxicity.

The data indicate that Span™ 80 can be used as a substitute for Span™ 60 and that the total surfactant in the formulation can be increased without causing phytotoxicity if Span™ 80 a component of the surfactant system

Example 5. Additional Phytotoxicity Studies

The formulations shown in Table 6 were prepared and tested as described in Example 2, except that phytotoxicity final injury ratings were made at 8 days after initial application rather than 7.

TABLE 6

Comparison of phytotoxicity to geranium and cucumber among different formulations.

| Experimental Formulation | Sunspray 6N Oil | Cab-O-Sil M-5 | Cirrasol G-1086 | Span 80 | % of NIS as Span | Geranium at 0.8% formulation (w/w) | Geranium at 1.6% formulation (w/w) | Cucumber at 0.8% formulation (w/w) | Cucumber at 1.6% formulation (w/w) |
|---|---|---|---|---|---|---|---|---|---|
| 1 | 56% | 3% | 27.75 | 2.25% | 7.5% | 0 | 0 | 0.00 e | 0.05 c |
| 2 | 56% | 3% | 30% | 0% | 0% | 0 | 0 | 0.00 e | 0.05 c |
| 3 | 56% | 3% | 28.5% | 0.3% | 1% | 0 | 0 | 0.01 d | 0.10 b |
| 4 | 56% | 3% | 27.75% | 0.75% | 2.5% | 0 | 0 | 0.05 c | 0.05 c |
| 5 | 56% | 3% | 28.5% | 1.5% | 5% | 0 | 0 | 0.10 b | 0.10 b |
| 6 | 56% | 3% | 27.75% | 2.25% | 7.5% | 0 | 0 | 0.10 b | 0.05 c |
| 7 | 56% | 3% | 27% | 3% | 10% | 0 | 0 | 0.05 c | 0.10 b |
| 8 | 56% | 3% | 25.5% | 4.5% | 15% | 0 | 0 | 0.00 e | 0.10 b |
| 9 | 56% | 3% | 24% | 6% | 20% | 0 | 0 | 0.20 a | 0.20 a |
| 10 | 56% | 3% | 22.5% | 7.5% | 25% | 0 | 0 | 0.05 c | 0.10 b |
| LSD (P = 0.10) | | | | | | | | | 0.000 |
| Standard Deviation | | | | | | | | | 0.000 |
| CV | | | | | | | | | 0.0 |
| Bartlett's X2 | | | | | | | | | 0.0 |
| P (Bartlett's X2) | | | | | | | | | |
| Skewness | | | | | | | | | 0.828 |
| Kurtosis | | | | | | | | | 0.3925 |
| Treatment F | | | | | | | | | 0.000 |
| Treatment Prob (F) | | | | | | | | | 1.0000 |

\* Means followed by the same letter among rows and columns for the two rates of the same plant type do not significantly differ (P = 0.05, Duncan's New MRT).
\*\* All formulations contained 11% *Metarhizium anisopliae* spores by weight.

To summarize the phytotoxicity studies, at lower concentrations of total surfactant, phytotoxicity decreases as the relative amount of Span™ 60 or the relative amount of Span™ 80 increases; whereas at higher concentrations of total surfactant, phytoxicity is low for all relative amounts of Span™ 60 or Span™ 80.

Example 6. Formation of Residues on Plastic

Formulations with different concentrations of Span™ 60 were prepared, as described in Example 2, and are shown in Table 7. The formulations were diluted to 0.4% w/w in artificial hard water. A concentrated stock solution (1 L) of hard water (nominally 1500 ppm $CaCO_3$) was prepared by dissolving 1.47 g of $CaCl_2.2H_2O$ (Fisher) and 1.02 g of $MgCl_2.6H_2O$ (Sigma Aldrich) in 997.52 g of DI water. Water hardness of the stock solution was checked using a Hach test kit (Model No. HA-71A). Typical hardness for the stock solution was 1500 ppm $CaCO_3$. The 342 ppm hard water test solution was prepared by appropriate dilution of the stock solution with DI water. A 100 mL sample of each 0.4% dilution was shaken at a setting of 10 on a Burrell model 75 wrist action shaker in a horizontal position for 15 minutes. Five individuals then ranked formulations by assigning a number of 1-14, with 1 having the least residue on the side of the bottle and 14 having the most residue on the side of the bottle. The average of these rankings is presented in Table 7 as "Residue on Plastic After Shaking". A 100 mL sample of each 0.4% dilution was stirred using a magnetic stirrer for 1 hour. Five individuals then ranked formulations by assigning a number of 1-14, with 1 having the least residue on the side of the bottle and 14 having the most residue on the side of the bottle. These sample bottles were also ranked for residues remaining on the surface of the water using the same 1-14 rating. The average of these rankings is presented in Table 7 as "Residue on Plastic After Stirring" and "Formulation Floating on Water Surface", respectively. The mean of these three rankings is presented in Table 7 as "Overall Residues Comparison".

TABLE 7

Comparison of residues remaining on plastic and separation among different formulations.

| Experimental Formulation | Sunspray 6N Oil | Cab-O-Sil M-5 | Cirrasol G-1086 | Span 60 | % of NIS as Span | Atlox Metasperse 550S | Residue on Plastic After Shaking (1-14) | Residue on Plastic After Stirring (1-14) | Formulation Floating on Water Surface (1-14) | Overall Residues Comparison |
|---|---|---|---|---|---|---|---|---|---|---|
| E without | 78 | 1 | 10 | 0 | 0 | 0 | 2.2 | 2.2 | 4.7 | 3.0 |
| E1 with 5%** | 78 | 1 | 9.5 | 0.5 | 5 | 0 | 8.2 | 4.4 | 4.1 | 5.6 |
| E2 with 10% | 78 | 1 | 9 | 1 | 10 | 0 | 7.4 | 8.5 | 10.2 | 8.7 |
| E3 with 15% | 78 | 1 | 8.5 | 1.5 | 15 | 0 | 12.2 | 10.6 | 10.4 | 11.1 |
| F without | 73 | 1 | 10 | 0 | 0 | 5 | 11.4 | 12.2 | 11.5 | 11.7 |
| F1 with 5% | 73 | 1 | 9.5 | 0.5 | 5 | 5 | 4.6 | 5 | 5.4 | 5.0 |
| F2 with 10% | 73 | 1 | 9 | 1 | 10 | 5 | 3.4 | 9.2 | 8.8 | 7.1 |
| F3 with 15% | 73 | 1 | 8.5 | 1.5 | 15 | 5 | 4.8 | 5.8 | 5.5 | 5.4 |
| G without | 68 | 1 | 10 | 0 | 0 | 10 | 9.4 | 5.8 | 6.0 | 7.1 |
| G1 with 5% | 68 | 1 | 9.5 | 0.5 | 5 | 10 | 7 | 7 | 7.2 | 7.1 |

TABLE 7-continued

Comparison of residues remaining on plastic and separation among different formulations.

| Experimental Formulation | Sunspray 6N Oil | Cab-O-Sil M-5 | Cirrasol G-1086 | Span 60 | % of NIS as Span | Atlox Metasperse 550S | Residue on Plastic After Shaking (1-14) | Residue on Plastic After Stirring (1-14) | Formulation Floating on Water Surface (1-14) | Overall Residues Comparison |
|---|---|---|---|---|---|---|---|---|---|---|
| G2 with 10% | 68 | 1 | 9 | 1 | 10 | 10 | 6.6 | 1.6 | 1.3 | 3.2 |
| G3 with 15% | 68 | 1 | 8.5 | 1.5 | 15 | 10 | 2.6 | 2.6 | 3.3 | 2.8 |

\* All formulations contained 11% *Metarhizium anisopliae* spores by weight.
\*\*Expressed as percent of surfactant made up by Span 60.

These studies indicate a range of residues for the various formulations. Residue amounts generally increased as the amount of Span™ 60 relative to the total amount of nonionic surfactant in the formulations increased.

In addition, similar residue studies were performed with the formulations shown in Table 6. Generally, the data showed increasing residues with increasing concentrations of Span™ 80 relative to the total amount of nonionic surfactant in the formulations. More specifically, for the tested formulations, which contained 30% total nonionic surfactant, the amount of residues visibly increased as the Span™ 80 in a formulation increased to above 10% of the total content of nonionic surfactant.

The invention claimed is:

1. A biopesticide comprising an agriculturally suitable carrier, a pesticidally effective amount of at least one fungal pesticide, at least one sorbitan fatty acid surfactant, and at least one sorbitol ethoxylate ester surfactant,
where a total amount of sorbitan fatty acid surfactant is between about 0.5 to about 7.5 wt. %, and a total amount of sorbitol ethoxylate ester surfactant is between about 7.5 to about 30 wt. % of the biopesticide,
where the sorbitan fatty acid surfactant includes a sorbitan monostearate or a sorbitan monooleate, and the sorbitol ethoxylate ester surfactant includes a polyoxyethylene sorbitol hexaoleate,
where the fungal pesticide includes *Alternaria cassiae, Fusarium lateritum, Fusarium solani, Verticillium lecanii, Aspergillus parasiticus, Metarhizium anisooliae* or *Beauveria bassiana;*
where the fungal pesticide is in the form of spores in the biopesticide;
where the fungal pesticide is viable in the biopesticide and does not have more than a 1-log loss in viability over a one-year period; and
when diluted with water at a rate of between about 5.00 g of biopesticide to 95.00 g of water, to about 0.01 g of biopesticide to 99.99 g of water, the dilution is well dispersed, does not clog a delivery apparatus when used to contact a plant, and causes minimal phytotoxic injury to the plant.

2. The biopesticide of claim 1, where the polyoxyethylene sorbitol hexaoleate includes a polyoxyethylene (40) sorbitol hexaoleate.

3. The biopesticide of claim 1, where a ratio of the sorbitan fatty acid surfactant to the ethoxylate ester surfactant is between about 0.02 to 1 to about 0.25 to 1.

4. The biopesticide of claim 1, where a total amount of surfactant is about 30 wt. % of the biopesticide, the sorbitan fatty acid surfactant includes a sorbitan monooleate, the sorbitol ethoxylate ester surfactant includes a polyoxyethylene (40) sorbitol hexaoleate, and a ratio between the sorbitan monooleate and the polyoxyethylene (40) sorbitol hexaoleate is about 0.08 to 1.

5. The biopesticide of claim 1, where the biopesticide includes an anti-settling agent.

6. The biopesticide of claim 5, where the anti-settling agent includes fumed silica.

7. The biopesticide of claim 1, where the agriculturally acceptable carrier includes a paraffinic oil.

8. The biopesticide of claim 1, where the at least one fungal pesticide includes a strain of *Metarhizium anisopliae* having a deposit accession number DSM 3884, a deposit accession number DSM 3885, or combinations thereof.

9. A biopesticide comprising an agriculturally suitable carrier, a pesticidally effective amount of a strain of *Metarhizium anisopliae*, a sorbitan fatty acid surfactant, and a sorbitol ethoxylate ester surfactant;
where the biopesticide is capable of being diluted in water to about 0.8 g of biopesticide to 99.2 g of water to provide a diluted biopesticide;
where the diluted biopesticide is able to be delivered without the *Metarhizium anisopliae* adhering/sticking to an inner wall of a delivery device and without a phytotoxic effect on a plant when the diluted biopesticide is applied to the plant,
where the sorbitan fatty acid surfactant includes a sorbitan monostearate or a sorbitan monooleate, and the sorbitol ethoxylate ester surfactant includes a polyoxyethylene sorbitol hexaoleate;
where the total amount of sorbitan fatty acid surfactant in the undiluted biopesticide is between about 0.5 to about 7.5 wt. %, and the total amount of sorbitol ethoxylate ester surfactant in the undiluted biopesticide is between about 7.5 to about 30 wt. %;
where the *Metarhizium anisopliae* is viable in the biopesticide and does not have more than a 1-log loss in viability over a one-year period, and
where the *Metarhizium anisopliae* is in the form of spores in the biopesticide.

\* \* \* \* \*